(12) United States Patent
Faustman

(10) Patent No.: US 8,021,693 B2
(45) Date of Patent: *Sep. 20, 2011

(54) METHODS OF ORGAN REGENERATION USING HOX11-EXPRESSING PLURIPOTENT CELLS

(75) Inventor: Denise L. Faustman, Boston, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/549,714

(22) Filed: Aug. 28, 2009

(65) Prior Publication Data

US 2010/0068177 A1    Mar. 18, 2010

Related U.S. Application Data

(63) Continuation of application No. 10/698,734, filed on Oct. 31, 2003, now Pat. No. 7,582,313, which is a continuation-in-part of application No. 10/358,664, filed on Feb. 5, 2003, now Pat. No. 7,628,988.

(60) Provisional application No. 60/392,687, filed on Jun. 27, 2002.

(51) Int. Cl.
    A61K 35/28    (2006.01)
    C12N 5/08    (2006.01)

(52) U.S. Cl. .................................... 424/577; 435/372

(58) Field of Classification Search .................. None
See application file for complete search history.

(56) References Cited

U.S. PATENT DOCUMENTS

| 7,015,037 B1 | 3/2006 | Furcht et al. |
| 7,510,877 B2 | 3/2009 | Yilmaz et al. |
| 2002/0187548 A1 | 12/2002 | Keller et al. |

FOREIGN PATENT DOCUMENTS

| WO | WO 97/21802 | 6/1997 |
| WO | WO 2004/003164 | 1/2004 |

OTHER PUBLICATIONS

Atkinson et al. Nature, 1999, V.5, pp. 601-604.*
Kaufman et al., J of Immunol. 1997, V.158, pp. 2435-2442.*
Feldman et al Transplant. Proc. 1998, 30, 4126-4127.*
Mestas et al ., J. of Immunology, 2004, 172, pp. 2731-3238.*
Dieguez-Acuna et al., "Characterization of Mouse Spleen Cells by Subtractive Proteomics," Mol. Cell. Proteomics 4(10):1459-1470, 2005.
Kodama et al., "Islet Regeneration During the Reversal of Autoimmune Diabetes in NOD Mice," Science 302:1223-1227, 2003.
Kodama et al., "Regenerative Medicine: A Radical Reappraisal of the Spleen," Trends Mol. Med. 11(6):271-276, 2005.
Ryu et al., "Reversal of Established Autoimmune Diabetes by Restoration of Endogenous β Cell Function," J. Clin. Invest. 108(1):63-72, 2001.
Supplementary Partial European Search Report for EP 04817543.4 (PCT/US2004/037998) (Oct. 19, 2009).
Al-Awquati and Oliver, "Stem Cells in the Kidney," Kidney Int. 61:387-395, 2002.
Brodbeck and Englert, "Genetic Determination of Nephrogenesis: The Pax/Eya/Six Gene Network," Pediatr. Nephrol. 19:249-255, 2004. (Abstract Only).
Cole et al., "Two ParaHox Genes, SpLox and SpCdx, Interact to Partition the Posterior Endoderm in the Formation of a Functional Gut," Development 136:541-549, 2009.
Dear et al., "The Hox11 Gene is Essential for Cell Survival During Spleen Development," Development 121:2909-2915, 1995.
Dieguez-Acuña et al., "Characterization of Mouse Spleen Cells by Subtractive Proteomics," Mol. Cell. Proteomics 4:1459-1470, 2005.
Dieguez-Acuña et al., "Proteomics Identifies Multipotent and Low Oncogenic Risk Stem Cells of the Spleen," Int. J. Biochem. Cell Biol 42:1651-1660, 2009.
Durand et al., "Mesenchymal Lineage Potentials of Aorta-Gonad-Mesonephros Stromal Clones," Heamatologica 91:1172-1179, 2006.
Hostikka and Capecchi, "The Mouse Hoxc11 Gene: Genomic Structure and Expression Pattern," Mech. Dev. 70:133-145, 1998. (Abstract Only).
Kodama et al., "Regenerative Medicine: A Radical Reappraisal of the Spleen," Trends Mol. Med. 11:271-276, 2005.
Koyama et al., "Hox11 Genes Establish Synovial Joint Organization and Phylogenetic Characteristics in Developing Mouse Zeugopod Skeletal Elements," Development 137:3795, 2010. (Abstract Only).
Murthi et al., "Novel Homeobox Genes are Differentially Expressed in Placental Microvascular Endothelial Cells Compared with Macrovascular Cells," Placenta 29:624-630, 2008. (Abstract Only).
Raju et al., "Characterization and Developmental Expression of Tlx-1, the Murine Homolog of HOX11," Mech. Dev. 44:51-64, 1993.
Roberts et al., "Developmental Expression of Hox11 and Specification of Splenic Cell Fate," Am. J. Pathol. 146:1089-1101, 1995.
Swirski et al., "Identification of Splenic Reservoir Monocytes and Their Deployment to Inflammatory Sites," Science 325:612-616, 2009.
Tamura et al., "In Vivo Differentiation of Stem Cells in the Aorta-Gonad-Mesonephros Region of Mouse Embryo and Adult Bone Marrow," Exp. Hematol. 30:957-966, 2002. (Abstract Only).
Wellik et al., "Hox11 Paralogous Genes are Essential for Metanephric Kidney Induction," Genes Dev. 16:1423-1432, 2002.
Wellik, "The Role of Hox11 Paralogous Genes in Prostate Development," Grant Detail, 2009. (Abstract Only).

* cited by examiner

Primary Examiner — Michail Belyavskyi
(74) Attorney, Agent, or Firm — Clark & Elbing LLP

(57) ABSTRACT

The invention features methods for increasing or maintaining the number of functional cells of a predetermined type in a mammal (e.g., a human patient), for example, the insulin producing cells of the pancreas, liver cells, spleen cells, or bone cells, that has injured or damaged cells of the predetermined type or is deficient in cells of the predetermined type.

25 Claims, 11 Drawing Sheets

A

B

B

C

A

B

METHODS OF ORGAN REGENERATION USING HOX11-EXPRESSING PLURIPOTENT CELLS

CROSS-REFERENCE TO RELATED APPLICATIONS

This application is a continuation of, and claims priority from, U.S. application Ser. No. 10/698,734, filed Oct. 31, 2003, now U.S. Pat. No. 7,582,313, which is a continuation-in-part of, and claims priority from, U.S. application Ser. No. 10/358,664, filed Feb. 5, 2003, now U.S. Pat. No. 7,628,988, which claims benefit of the filing date of U.S. Provisional Application No. 60/392,687, filed Jun. 27, 2002, each of which is incorporated by reference herein in their entirety.

BACKGROUND OF THE INVENTION

The invention relates to repairing and regenerating damaged tissue in a mammal (e.g., a human patient). Such damage may result from an existing autoimmune disease, or may be the result of a non-autoimmune insult. I have previously shown that eliminating autoimmune cells and re-educating the immune system are important components of an effective treatment of an autoimmune disease (described in U.S. patent application Ser. Nos. 10/358,664, 09/521,064, 09/768,769, and Ryu et al., *Journal of Clinical Investigations*, 108: 31-33, 2001, which are hereby incorporated by reference herein). While an autoimmune disease may be successfully treated, the individual may nonetheless have significant tissue damage as a result of the prior autoimmune attack.

Many tissues have an innate ability to repair themselves once the damage causing insult is eliminated, but this ability to repair damage decreases in correlation with the duration of the insult. For example, the regenerative capacity of endogenous pancreatic islets is virtually eliminated in long-term Type I diabetics, i.e., patients who have had the disease for more than 15 years. In cases where the endogenous tissue has lost its regenerative capacity, the damage may be repaired by providing exogenous tissue to the individual, for example, by a transplant. A promising treatment for diabetes, islet transplantation, has been the subject of human clinical trials for over ten years. While there have been many successes with islet transplantation in animals, these have occurred where the animals are diabetic due to chemical treatment, rather than natural disease. The only substantiated peer reviewed studies using non-barrier and non-toxic methods and showing success with islet transplants in naturally diabetic mice use isogeneic (self) islets. The isogeneic islets were transplanted into non-obese diabetic (NOD) mice with active diabetes, which were pre-treated with TNF-alpha (tumor necrosis factor-alpha); BCG (*Bacillus* Clamette-Guerin, an attenuated strain of mycobacterium bovis); or CFA (Complete Freund's Adjuvant), which is an inducer of TNF-alpha (Rabinovitch et al., *J. Immunol.* 159: 6298-6303, 1997). This approach is not clinically applicable primarily because syngeneic islets are not available. Furthermore, existing cell replacement strategies have not prevented end-stage diseases or permanently reversed insulitis. In the allograft setting of islet transplantation, grafts are eventually rejected, even with immunosuppression. Furthermore, diabetic host treatments such as body irradiation and bone marrow transplantation are unacceptably toxic, rendering the short-term alternative of insulin therapy more attractive.

Recently, islet transplantation has achieved limited success in clinical trials, with type 1 diabetic patients having a sustained return to normoglycemia over a 6 month period. These results have been obtained with continuous, and sometimes toxic, drug therapy, often in the setting of a simultaneous life-saving renal transplant. However, these moderately successful islet transplants show failures after about one year, speculated to be due in part to the drug therapy itself inducing insulin resistance. The earlier failure of islet transplants in type 1 diabetics, compared to non-diabetic patients receiving islet transplants (such as in cancer patients who have had their pancreas removed), raises the concern that immunosuppressive therapy shows greater efficacy for graft rejection over autoimmunity prevention. Lending credence to these concerns is the observation of the inefficiency of immunosuppression therapy for the prevention of graft rejection of allogenic or xenogeneic islet transplants in animal studies using non-obese diabetic (NOD) mice.

I have previously described a transplantation method to introduce allogeneic and xenogeneic tissues into non-immunosuppressed hosts in which the cells are modified such that the donor antigens are disguised from the host's immune system (U.S. Pat. No. 5,283,058, which is hereby incorporated by reference). Generally, masked islets or transgenic islets with ablated MHC class I molecules are only partially protected from recurrent autoimmunity in NOD mice (Markmann et al., *Transplantation* 54: 1085-89, 1992). It has also been shown that a brief two-component therapy is able both to reestablish self-tolerance and to eliminate selectively the pathological memory T cells of NOD mice by the induction of apoptosis (Ryu et al., *Journal of Clinical Investigations*, 108: 31-33, 2001). Simultaneous treatment of severely diabetic animals with TNF-α (or an inducer of endogenous TNF-α production) and with splenocytes partially or fully matched with regard to MHC class I antigens (to reselect pathogenic naïve T cells) thus results in permanent reversal of established diabetes. This "cure" is accompanied by the reappearance of insulin-secreting islets in the pancreas of treated animals that are able to control blood glucose concentration in a manner indistinguishable from that apparent in normal mice.

The existence of pluripotent stem cells in the bone marrow of adult mammals has been well documented. The existence of pluripotent cells that reside outside the bone marrow has also been demonstrated (Kuehnle and Goodell, *Br. Med. J.* 325: 372-6; 2002; Rosenthal, *New Eng. J. Med.* 349: 267-74; 2003). Studies in both mice and in humans have shown that the introduction of MHC-matched bone marrow cells into irradiated hosts results both in repopulation of the host bone marrow as well as rare examples of donor engraftment of host parenchymal organs, including the liver, brain, muscle, and heart, with scattered tissue-specific cells. Such engraftment is typically neither robust nor durable, however. In culture, pluripotent cells are also able to differentiate into mesoderm, neuroectoderm, and endoderm (Jiang et al., *Nature* 418: 41, 2002). Presumably, the nonlymphoid cells of donor origin in the transplantation studies are the product of transdifferentiation, the conversion of one adult cell type to another. Furthermore, cultured adult bone marrow stem cells may fuse, albeit at a low frequency, with co-cultured embryonic cells. More robust fusion events occur in the remaining liver tissue in a mouse model of liver damage after total host body irradiation and transplantation of bone marrow cells. However, such fusion generates cells with marked chromosomal abnormalities and does not represent transdifferentiation or developmental plasticity. Concerns have also been raised about the functionality or malignant potential of some cultured pluripotent cells or their in vivo fusion derivatives if the stem cells are to be used for therapeutic purposes in humans.

A need exists for methods of regenerating damaged tissue using adult pluripotent cells. Desirably, the pluripotent cells need little or no damaging pre-treatment (such as, for example, irradiation or chemical treatment), or are from an endogenous source and are induced or stimulated. Ideally, the regeneration methods would not only be applicable to tissue damage that results from autoimmune attack, but also to non-autoimmune induced damage.

SUMMARY OF THE INVENTION

The invention features methods for organ or tissue regeneration in a mammal (e.g., a human patient). Accordingly, in a first aspect, the invention features a method for increasing or maintaining the number of functional cells of a predetermined type in an organ or tissue of a mammal who has injured or damaged cells of the predetermined type, or is deficient in the predetermined type of cells, that includes administering to the mammal a composition enriched in pluripotent cells that express the Hox11 gene.

In one embodiment, the organ or tissue is stimulated prior to administering the pluripotent cell composition. Stimulation can include the use of agents that damage or otherwise prepare the organ or tissue for new cell growth. Stimulating agents include TNF-alpha, TNF-alpha agonists, or TNF-alpha inducing substances such as, for example, complete Freund's adjuvant (CFA), ISS-ODN, microbial cell wall components with LPS-like activity, cholera particles, *E. coli* heat labile enterotoxin, *E. coli* heat labile enterotoxin complexed with lecithin vesicles, ISCOMS-immune stimulating complexes, polyethylene glycol, poly(N-2-(hydroxypropyl) methacrylamide), synthetic oligonucleotides containing CpG or CpA motifs, monophosphoryl lipid A, MPL, *Bacillus* Clamette-Guerin, γ-interferon, Tissue Plasminogen Activator, LPS, Interleukin-1, Interleukin-2, UV light, a lymphotoxin, cachectin, a TNFR-2 agonist, an intracellular mediator of the TNF-alpha signaling pathway, a NFκB inducing substance, IRF-1, STAT1, a lymphokine, or the combination of TNF-alpha and an anti-TNFR-1 antibody. Preferably, the stimulating agent is TNF-alpha, BCG, gamma-interferon, or CFA. Stimulating agents can be administered any time prior to, preferably 6-12 hours before, administration of the pluripotent cell composition In another embodiment, the therapeutic composition is enriched in cells that do not express CD45 protein. Such a composition is obtained by providing mammalian peripheral blood or tissue containing pluripotent cells, separating the pluripotent cells from the blood or tissue, further separating the pluripotent cells into a first cell population that predominantly expresses CD45 protein (i.e., one that is predominantly $CD45^+$) on the cell surface and a second cell population that predominantly does not express CD45 protein (i.e., one that is predominantly $CD45^-$) on the cell surface, and selecting the second cell population. A cell population that is predominantly $CD45^-$ is one that contains more cells that do not express this protein on the cell surface than those that do. Desirably, at least 75%, more desirably, at least 90%, and most desirably, at least 95% of the second cell population is populated with cells that do not express CD45. $CD45^-$ cell populations are obtained by removing those cells expressing CD45 through the use of affinity chromatography or by cell sorting techniques.

The pluripotent cells used in the methods of the present invention can be derived from spleen cell populations. In other embodiments, the pluripotent cells can be semi-allogeneic or isogeneic. In yet another embodiment, Hox 11 expression in a pluripotent cell population can be induced ex vivo, followed by administration of the Hox 11-pluripotent cell composition to the mammal. In the methods of the invention, the pluripotent cell compositions can be administered one or more times. Typically, the compositions are added daily, twice weekly, or weekly, the frequency of administration dependent upon the treated subject's response to therapy (i.e., the successful regeneration of organs or tissue of the predetermined type).

In another aspect, the methods of the invention are used to treat damage or deficiency of cells in an organ, muscle, or other body structure or to form an organ, muscle, or other body structure. Desirable organs or tissue include the pancreas, islets of Langerhans, spleen, liver, kidney, bone, blood, vascular tissue, brain, spinal cord, nervous system tissue, heart, bile duct, skin, bladder, eye, stomach, intestines, muscle, ligament, cartilage, gut, esophagus, fallopian tube, gallbladder, lung, ovaries, prostate, testes, thymus, thyroid, trachea, ureter, urethra, uterus, and fat.

In another aspect, the invention features a method for increasing or maintaining the number of functional cells of a predetermined type in an organ or tissue of a mammal who has injured or damaged cells of the predetermined type, or is deficient in the predetermined type of cells, that includes administering to the mammal a composition that contains pluripotent cells resulting from transfection of a pluripotent or totipotent cell, preferably a semi-allogeneic or isogeneic pluripotent cell, with a Hox 11 gene, preferably a human Hox 11 gene. Preferably, transfection of the pluripotent cell results in the expression of the Hox11 gene. In one embodiment, the pluripotent cells are splenocytes or are obtained from cord blood. In another embodiment, the transfected cell is capable of differentiating into a pancreatic cell, a spleen cell, a liver cell, a kidney cell, or a bone cell, most preferably a pancreatic cell. In yet another embodiment, the transfected cells are $CD45^-$.

Any of the compositions of the invention can further include moieties (e.g., cells) that present MHC class I and peptide, where the MHC class I has at least one allele that matches an MHC class I allele expressed by the mammal to whom the composition is administered to and the peptide is one that is derived from endogeneous cells of the mammal.

In another aspect, the invention features a method for increasing or maintaining the number of functional cells of a predetermined type in an organ or tissue of a mammal who has injured or damaged cells of the predetermined type, or is deficient in the predetermined type of cells, that includes administering to the mammal an agent that induces and/or stimulates Hox 11-expressing pluripotent cells in which the Hox11 gene is expressed. In one embodiment, the Hox 11-expressing cells are not bone marrow cells.

In another embodiment, the agent is gene therapy vector comprising a Hox 11 gene operably linked to a promoter where the vector induces the expression Hox 11 in the pluripotent cells.

In another embodiment, suitable agents are, or are those that induce or stimulate cytokines, chemokines, or growth factors, which in turn induce or stimulate Hox 11-expressing pluripotent cells. Examples of these agents can be selected from the group consisting of epidermal growth factor (EGF), platelet-derived growth factor (PDGF), fibroblast growth factors (FGFs), transforming growth factor-beta (TGF-β), transforming growth factor-alpha (TGF-α), vascular endothelial growth factor (VEGF), erythropoietin (Epo), insulin-like growth factor-I (IGF-I), insulin-like growth factor-II (IGF-II), interleukins, tumor necrosis factor-alpha (TNF-α), tumor necrosis factor-beta (TNF-β), gamma-interferon (INF-γ), stromal cell-derived factor-1 (SDF-1), and colony stimulating factors (CSFs).

In another embodiment, Hox 11-expressing pluripotent cells are quantitated before and after administration of the stimulating/inducing agent to the mammal. Quantitation can be aided by detecting a first marker, preferably a marker that is the result of Hox 11 gene expression, in the Hox 11-expressing cells and a second marker expressed by a control cell population or a second pluripotent cell population that is different from the Hox 11-expressing pluripotent cells. The method used to detect the first marker can include the use of an antibody specific for the marker, preferably with a binding constant for the marker of 1.0 µM or less. The relative increase or decrease of Hox 11-expressing cells can be assessed by comparing the ratios of first marker to second marker both before and after administration of the composition. If it is determined that administration of the Hox11-stimulating/inducing agent does not result in an increase of Hox11-pluripotent cells, then an additional amount of the same stimulating/inducing agent, or a different stimulating/inducing agent, can be administered to the mammal.

In another aspect the invention features a method for increasing or maintaining the number of functional cells of a predetermined type in an organ or tissue of a mammal who has injured or damaged cells of the predetermined type, or is deficient in the predetermined type of cells, that includes administering to the mammal an agent that selectively inhibits (e.g. via induction of senescence), removes, or kills cell populations that interfere or prevent the trafficking of, differentiation of, or growth of pluripotent cells. The pluripotent cells can be isogeneic or semi-allogeneic. Preferably, these cells express Hox-11. Repeat administration of the agent, or the administration of different agents, can then be affected as needed during therapy. In one example, the levels of lymphocytes with an increased sensitivity to apoptosis (e.g., those deficient in the expression of CD180) can be assessed by obtaining a blood sample from the patient and quantitating the sensitive cells by techniques known to those skilled in the art, such as, for example, by FACS analysis. The agent or agents can then be added as required to reduce or eliminate the lymphocytes that are apoptotically sensitive.

Any of the methods of the present invention can further include the inducement of damage to organ or tissue cells of a predetermined type prior to administering the pluripotent cell composition. Methods of the present invention can also include administering to the mammal, before, during or after the administration of a Hox 11-expressing pluripotent cell composition or an agent that stimulates or induces Hox 11-expressing pluripotent cells, the administration of an agent that can selectively inhibit, remove, or kill cell populations that interfere or prevent the trafficking, differentiation, or growth of pluripotent cells. As before, repeat administration of the agent, or the administration of different agents, can then be affected as needed during therapy.

Agents that can selectively inhibit, remove, or kill cell populations (e.g., lymphocytes) that interfere or prevent the trafficking, differentiation, or growth of pluripotent cells include TNF-alpha, TNF-alpha agonists, or TNF-alpha inducing substances such as, for example, complete Freund's adjuvant (CFA), ISS-ODN, microbial cell wall components with LPS-like activity, cholera particles, *E. coli* heat labile enterotoxin, *E. coli* heat labile enterotoxin complexed with lecithin vesicles, ISCOMS-immune stimulating complexes, polyethylene glycol, poly(N-2-(hydroxypropyl)methacrylamide), synthetic oligonucleotides containing CpG or CpA motifs, monophosphoryl lipid A, *Bacillus* Clamette-Guerin, γ-interferon, Tissue Plasminogen Activator, LPS, Interleukin-1, Interleukin-2, UV light, a lymphotoxin, cachectin, a TNFR-2 agonist, an intracellular mediator of the TNF-alpha signaling pathway, a NFκB inducing substance, IRF-1, STAT1, a lymphokine, or the combination of TNF-alpha and an anti-TNFR-1 antibody. Preferably, the agent is TNF-alpha, CFA, gamma-interferon, or BCG.

Any of the methods of the present invention can be used to treat a mammal (e.g., a human patient) who has an autoimmune disease, for example, diabetes, immunologically-mediated glomerulonephritis, chronic hepatitis, primary biliary cirrhosis, or primary sclerosing cholangitis.

DEFINITIONS

By "autoimmune disease" is meant a disease in which an immune system response is generated against self epitopes. Some examples of autoimmune diseases include Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, Discoid Lupus, Essential Mixed Cryoglobulinemia, Fibromyalgia-Fibromyositis, Graves' Disease, Guillain-Barré, Hashimoto's Thyroiditis, Hypothyroidism, Idiopathic Pulmonary Fibrosis, Idiopathic Thrombocytopenia Purpura (ITP), IgA Nephropathy, Insulin dependent Diabetes, Juvenile Arthritis, Lichen Planus, Lupus, Ménière's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjögren's Syndrome, Stiff-Man Syndrome, Takayasu Arteritis, Temporal Arteritis/Giant Cell Arteritis, Ulcerative Colitis, Uveitis, Vasculitis, Vitiligo, Wegener's Granulomatosis, and myasthenia gravis.

In the present invention, MHC class I and peptide complexes can be used for the restoration of T-cell selection by the elimination of pathogenic (e.g., autoimmune) T cells. As used herein, the term "MHC class I and peptide" includes naturally occurring complexes (i.e., MHC complexes with native antigen-derived peptides) and complexes with peptides that differ from native antigen-derived peptides but which are nonetheless able to form a complex with class I that is effective to maintain functional cells according to the invention. Exemplary peptides that differ from native antigen-derived peptides may contain unnatural amino acids, e.g., D-amino acids, as well as naturally-occurring amino acids. Useful MHC peptide complexes include those that are linked complexes for crosslinking more than one host T cell receptor. Linked complexes may have higher affinity and thus be more effective in the removal of autoreactive T cells. MHC class I and peptide complexes can also include MHC fragments composed of the exterior binding groove but with removed or altered conserved regions. MHC class I and self peptide complexes have been crystallized and the resulting crystalline structure used to form soluble compounds with binding to the T cell receptor that is identical to or approximates that of the native complex. These soluble compounds can also be used in the methods of the invention.

Preferred MHC class I and peptide complexes are those in which a chain of amino acids between 8 and 10 residues in length is correctly complexed with an MHC class I molecule that is either semi-allogeneic, i.e., at least one MHC class I allele is mismatched and at least one MHC class I allele is matched between donor and recipient, or syngeneic, i.e., all MHC class I alleles are matched between donor and recipient, where the MHC class I and peptide complex contributes to the re-education or re-selection of the immune system.

MHC class I and self peptide complexes can be harvested from normal lymphoid cells. Alternatively MHC class I and self peptide complexes can be expressed in E. coli or eukaryotic cells and then refolded with antigenic peptides in vitro prior to administration. In some embodiments, the MHC class I and peptide are present on the surface of cells that are administered to the patient. Other MHC class I and peptide complexes are soluble complexes that are not expressed on the surface of a cell. In particular embodiments, the extracellular region of MHC class I (e.g., a Fab fragment of MHC class I) or soluble, full-length MHC class I is incubated with one or more peptides according to known methods under conditions that allow a peptide to bind the MHC class I fragment, and the resulting MHC class I and peptide complex is administered to the patient. In other embodiments, a mixture of MHC class I and peptide are administered to the patient, and the MHC class I and peptide bind in vivo after administration to the patient or multiple MHC class I and peptide complexes are administered. In some embodiments, the administered MHC class I has 1, 2, 3, or 4 alleles with at least 60, 70, 80, 90, 95, or 100% sequence identity to that MHC class I expressed by the patient. Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications.

By "functional cell," is meant cells that carry out their normal in vivo activity. In certain desirable embodiments of the invention, the cells are capable of expressing endogenous self-peptide in the context of MHC class I.

By "predetermined type," when used in reference to functional cells, is meant a defined cell type. For example, one skilled in the art may decide to carry out the method of the present invention in order to increase or maintain the number of functional islet cells in the pancreas. In this example, the cells of a predetermined type are islet cells or islet precursor cells.

Standard assays can be used to determine whether administered cells form cells of the predetermined cell type in vivo. For example, cells may be analyzed for expression of particular proteins (e.g., proteins specific for the predetermined cell type) using standard Western or immunofluorescence analysis or for the expression of particular mRNA molecules (e.g., mRNA molecules specific for the predetermined cell type) using a cDNA array (Ausubel et al., Current Protocols in Molecular Biology, John Wiley & Sons, New York, 2000). Examples of other characteristics of the administered cells that may be analyzed to determine whether they have been converted into the desired cell type include the size of the cell, cell morphology, volume of cytoplasm, and cell function (e.g., production of insulin or other hormones).

By "semi-allogeneic," is meant a match of at least one marker, for example, an MHC class allele, between cells of the same type from different individuals of the same species. Desirably at least two or three MHC class I alleles match between the donor and the host. Standard methods may be used to determine whether an MHC class I allele expressed by a donor cell matches an MHC class I allele expressed by the recipient. For example, antibodies specific for a particular MHC class I allele can be used to determine what alleles are expressed. Alternatively, PCR amplification of nucleic acids encoding MHC class I alleles can be used.

By "syngeneic donor cell" or "isogeneic donor cell," is meant (i) a donor cell that is genetically identical, or matched at the HLA region (i.e., has at least four, and preferably all 6, of the standard markers in common with), to a cell of the recipient or (ii) a donor cell that is re-administered to the same patient from which it was obtained.

A "TNF-alpha inducing agent," is desirably a compound that results in the expression of endogenous TNF-alpha, enhances secretion of TNF-alpha, or enhances bioavailability or stability of TNF-alpha. However, TNF-alpha agonists, agents that stimulate TNF-alpha signaling or enhance post-receptor TNF-alpha action, or agents that act on pathways that cause accelerated cell death of autoimmune cells, are also included in this definition. Stimulation of TNF-alpha induction (e.g., by administration of CFA) is desirably carried out prior to, after, or during administration (via implantation or injection) of cells in vivo.

Similarly, other "inducing agents" may cause the expression of a gene product, either through activation of a silent gene in an endogenous cell or by the insertion of an exogenous gene into an endogenous cell (e.g., via a gene therapy approach). Gene therapy approaches are known to those skilled in the art (e.g., see U.S. Pat. No. 6,384,202).

By "selectively killing blood cells" is meant directly or indirectly reducing the number or relative percentage of a subpopulation of blood cells (e.g., autoreactive lymphoid cells such as T- or B cells or the defective antigen presenting cells) such as a subpopulation of unstimulated cells or stimulated cells. In desirable embodiments, the subpopulation is a subset of T-cells, B-cells, or macrophages. Desirably, the killed memory T-cells are autoimmune T-cells, i.e., T-cells that are activated by presented self epitopes. In desirable embodiments, the killed naïve T-cells are cells that would otherwise become autoimmune T-cells. Desirably, the number of autoimmune T-cells or cells that would otherwise become autoimmune T-cells decreases by at least 25, 50, 100, 200, or 500% more the number of healthy non-autoimmune T-cells decreases. In some embodiments, the number of autoimmune T-cells or cells that would otherwise become autoimmune T-cells decreases by at least 25, 50, 75, 80, 90, 95, or 100%, as measured using standard methods. The T-cells can be killed due to any pathway, such as apoptosis, necrosis, and/or activation induced cell death. Apoptosis can be assayed by detecting caspase-dependent cell shrinkage, condensation of nuclei, or intranuclear degradation of DNA. Necrosis can be recognized by caspase-independent cell swelling, cellular degradation, or release of cytoplasmic material. Necrosis results in late mitochondrial damage but not cytochrome C release. In some embodiments, memory T-cell are killed by apoptosis, and naive T-cells are killed by necrosis. For the treatment of lupus, B-cells are desirably killed or, alternatively, they are allowed to developmentally mature.

By "stimulated blood cell" is meant a blood cell (e.g., a memory T-cell, a B-cell, or a macrophage) that has been exposed to an antigen.

By "unstimulated blood cell" is meant a blood cell (e.g., a naïve T-cell, a B-cell, or a macrophage) that has not been exposed to an antigen.

As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety of lineages (albeit not all lineages). A "pluripotent population of cells" refers to a composition of cells capable of developing into less than all lineages of cells but at least into all hematopoietic lineages. By definition, a totipotent cell or composition of cells is less developed than a pluripotent cell or compositions of cells.

DETAILED DESCRIPTION

Figure 1:
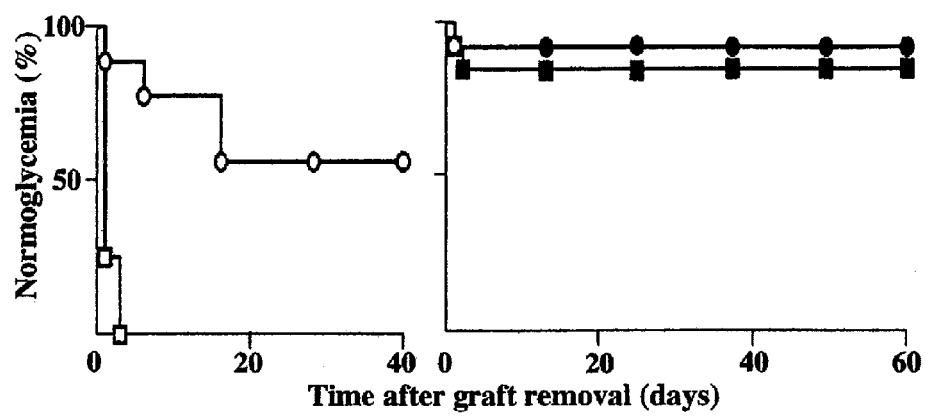
FIG. 1 shows the effects of treatment with live or irradiated splenocytes on the restoration of normoglycemia and pancreatic histology in diabetic NOD mice. (A) Kaplan-Meier curves for normoglycemia. Diabetic NOD females were treated with a single injection of CFA and biweekly injections for 40 days of either live (circles) or irradiated (squares) splenocytes from CByB6F1 males. Syngeneic female islets transplanted subrenally at the onset of treatment were removed after either 40 days (left panel) or 120 days (right panel). Blood glucose concentration was monitored at the indicated times after islet graft removal, and the percentage of animals that remained normoglycemic was plotted. Data are from 9 or 8 (left panel) or from 12 or 13 (right panel) animals that received live or irradiated splenocytes, respectively; P=0.0002 (left panel), P=0.68 (right panel) for comparison between the two treatment groups. (B) Pancreatic histology. NOD mice treated with live (right panels) or irradiated (middle panels) splenocytes and subjected to removal of the islet graft after 40 days as described in (A) were killed 80 days after treatment onset or after the return of hyperglycemia, respectively. Pancreatic sections were subjected to staining with hematoxylin-eosin (top panels) or to immunofluorescence analysis (green) with antibodies to CD45 (bottom panels). The pancreas of an untreated NOD female (25 weeks of age) after the onset of mild hyperglycemia is also shown (left panels). The distinctive histological patterns of invasive insulitis (left panels), peri-insulitis (middle panels), and minimal peri-insulitis (right panels) are apparent. Arrows indicate the outline of an islet. Original magnification, ×200. (C) Pancreatic histology. Three NOD mice successfully treated with either irradiated (top panels) or live (bottom panels) splenocytes were killed ~9 weeks after removal of the 120-day islet graft. Sections of each pancreas were stained with hematoxylin-eosin. Pronounced peri-insulitis was apparent only in the NOD mice treated with irradiated cells. Original magnification, ×200.
Figure 1:
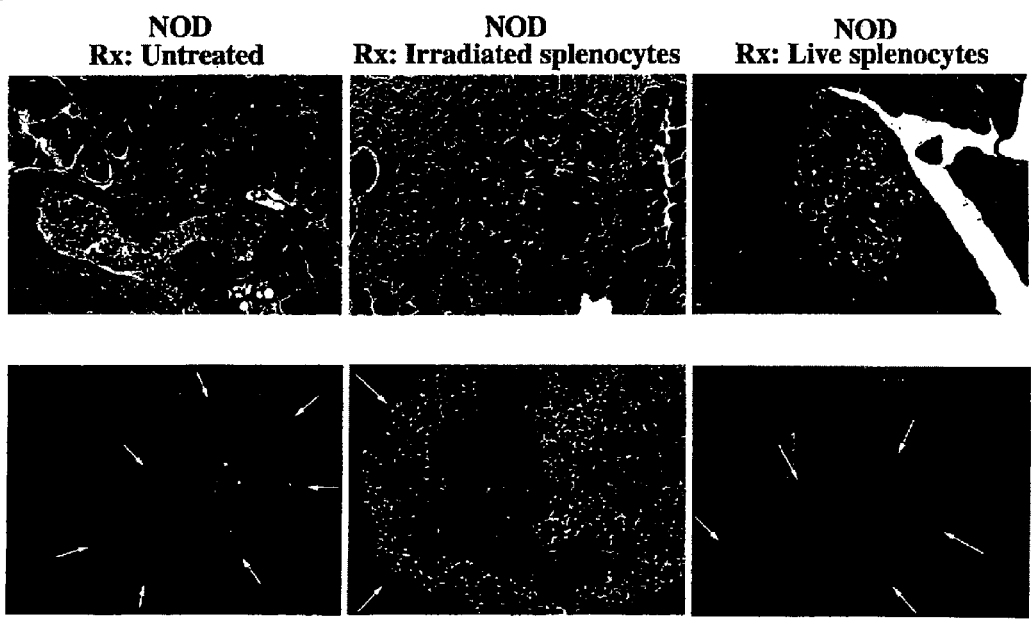
Figure 1:
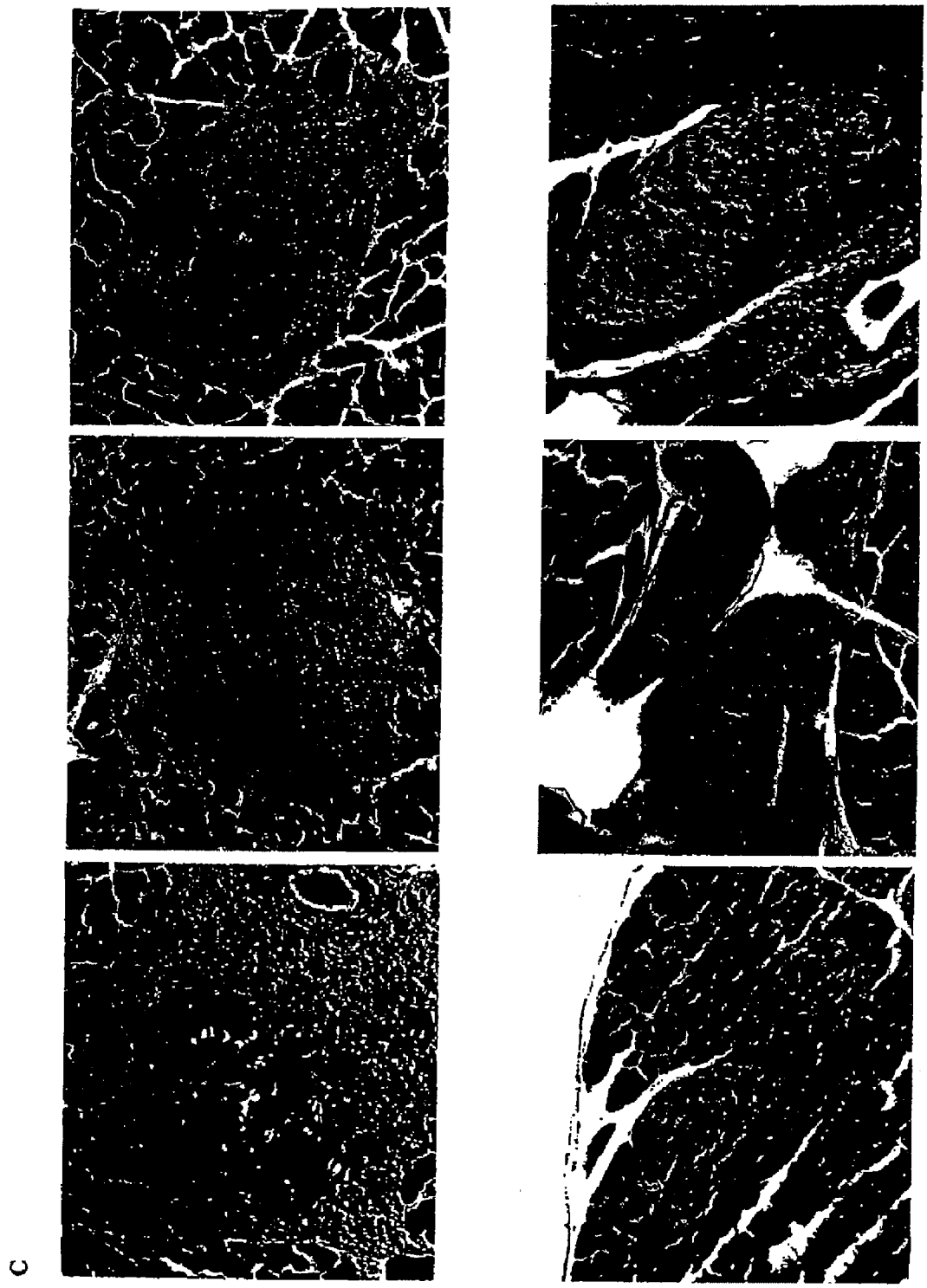

The treatment protocol for the restoration of near-normal pancreatic islet histology and long-term reversal of hyperglycemia in adult diabetic NOD mice (H-2K$^d$D$^b$) has been optimized since its initial description (Ryu et al., *Journal of Clinical Investigations*, 108: 31-33, 2001) to include both a 40-day regimen of biweekly injections of splenocytes either partially (C57BL/6; H-2K$^b$D$^b$) or fully (CByF1B6F$_1$/J (CByB6F1); H-2K$^b$K$^d$D$^b$D$^d$) matched for MHC class I antigens as well as either the repeated administration of TNF-α or a single injection of complete Freund's adjuvant (CFA), the latter of which induces the production of endogenous TNF-α and other cytokines. Preferably, the donor splenocytes are matched for at least one MHC class I molecule, and more preferably with two matching MHC class I alleles. The efficacy of this therapy can also be increased by concomitant euglycemia, which can be achieved by a transplant of syngeneic islets, an intraperitoneal transplant of alginate-encapsulated islets, or by the appropriate administration of insulin.

The reversal of autoimmunity in end-stage diabetic NOD mice was accompanied by the reappearance of functional islets in the pancreas. Female NOD mice treated with live semiallogeneic splenocytes manifested the stable transdifferentiation of male spleen-derived cells into mature islet parenchymal cells. No evidence of engraftment, transdifferentiation, or fusion of male splenocytes in organs including the brain, liver, and kidney was observed, suggesting that, in addition to the low level of hematopoetic chimerism observed, the marked incorporation of donor cells is selective for the diseased pancreas.

Therefore, I have found that, in addition to their contribution to the reversal of autoimmunity, donor splenocytes can also contribute directly to the regeneration of pancreatic islets in a NOD mouse host by manifesting the stable transdifferentiation of spleen-derived cells from an adult into mature islet parenchymal cells, resulting in a treatment protocol for diabetes in a mammal whose successful outcome is solely due to insulin secretion from the host pancreas.

I have also found that the administration of pluripotent cells in which the Hox11 gene is expressed, but which do not express CD45 protein, both mediate the education of naïve T cells through the presentation of self antigens and undergo differentiation into islet cells.

Embryonic stem cells are multipotent in that they are able to differentiate into endothelial and endoderm cells and they lack surface expression of CD45. The pancreas is formed after embryonic day (E) 9.5 in the mouse as a result of the proliferation of endodermal epithelial cells and the invasion by these cells of the surrounding mesenchyme. The adjacent spleen is derived from splanchnic mesoderm, and expression of the Hox11 homeobox gene is obligatory for the differentiation of splenic pluripotent cells (Roberts et al., *Nature* 368: 747-9, 1994). Mice deficient in Hox11 lack a spleen; the corresponding stem cells alter their differentiation pathway and contribute instead to pancreatic development (Kanzler et al., *Dev. Biol.* 234: 231-43, 2001).

Data presented herein show that diabetic NOD mice treated with irradiated splenocytes exhibit long-term restoration of normoglycemia, but with markedly slower kinetics than those apparent in the NOD animals treated with live splenocytes, suggesting that adult diabetic NOD mice contain endogenous precursor cells capable of giving rise to new syngeneic islet structures after the underlying autoimmune disease is eliminated.

Data also presented herein indicate that donor CD45$^+$ splenocytes, although essential for disease reversal as a result of their contribution of MHC class I and self peptide complexes, do not contain cells able to participate directly in islet generation.

It is therefore proposed that the rapid regeneration of islet cells in diabetic NOD mice treated with live splenocytes, compared with the slower islet regeneration dependent on endogenous cells (apparent in NOD hosts that receive irradiated cells), is due to the mobilization of pluripotent cells present in the donor spleen cells, and that live donor splenocytes thus not only contributed to reversal of autoimmunity, presumably by mediating the education of naïve T cells through presentation of self antigens, but also provided cells (Hox11$^+$ CD45$^-$ precursor cells) that undergo differentiation into islet cells.

The studies with the NOD mouse described in the present examples may have implications for treatment of diabetes or other autoimmune diseases in humans. The ability of an exogenous population of adult spleen cells to correct established diabetes permanently, as well as the presence of an endogenous population of NOD mouse stem cells able to give rise to new islets, indicates that therapies to reverse autoimmune diabetes need not incorporate transplantation of exogenous adult islets.

Materials and Methods

Animals, cells, and disease treatment. NOD female mice (Taconic Farms, Germantown, N.Y.) as well as male CByF1B6F$_1$/J(CByB6F1) mice (The Jackson Laboratory, Bar Harbor, Me.) were maintained under pathogen-free conditions. NOD females were screened for the onset of diabetes by the monitoring of body weight and blood glucose, with the diagnosis of diabetes after weight loss accompanied by two consecutive blood glucose concentrations of >400 mg/dL. Diabetes occurred in ~80% of females by 40 weeks of age in the NOD colony during the present study. At the end stage of diabetes, pancreatic histology revealed the almost complete elimination of identifiable islet structures, as well as elimination of clusters of insulitis that might obscure underlying damaged islets (Table 1, FIG. 5D).

Splenocytes for treatment of NOD females were derived from CByB6F1 (H-2K$^b$K$^d$D$^b$D$^d$) male mice. For irradiation, splenocytes were subjected to 30 Gy of ionizing radiation from a $^{137}$Cs source. Splenocytes (9×10$^6$) were injected into NOD recipients (H-2K$^d$D$^b$) through the tail vein twice a week for 40 days. Complete Freund's Adjuvant (CFA, Difco, Detroit, Mich.) was freshly mixed with an equal volume of physiological saline and then injected (50 μL) into each hind foot pad at the time of islet transplantation or simultaneously with the first splenocyte injection. The induction of endogenous TNF-α by CFA is as effective as is direct TNF-α administration in this model.

The separation of CD45$^+$ and CD45$^-$ spleen cells from CByB6F1 donor mice was achieved by isolation of the former cells with the use of mouse-specific CD45 MicroBeads (Miltenyi Biotec, Auburn, Calif.) from total spleen tissue that was mechanically teased apart with forceps. The CD45$^+$ or CD45$^-$ splenocytes (4×10$^5$ to 5×10$^5$) were injected into prediabetic NOD females twice a week for 2 weeks. The recipients also received a single injection of CFA and their blood glucose concentrations were monitored for 120 days or 17 weeks.

Enhanced green fluorescent protein (GFP)-transgenic male (+/−) mice (C57BL/6-TgH(ACTbEGFP)10sb) were purchased (The Jackson Laboratory, Bar Harbor, Me.) and breed to BALB/c female mice to produce some male F1 offspring of the CByB6F1-GFP genotype. GFP transgenic mouse with an "enhanced" GFP cDNA under the control of a chicken beta-actin promoter and cytomegalovirus enhancer make most but not all tissues appear green with only excitation light (JaxMice Data Sheet, Bar Harbor, Me.). Islets of Langerhans for GFP illumination require anti-GFP antibodies for immunohistochemistry and had minimal autofluorescence with excitation.

Islet transplantation. Islet transplantation for the temporary maintenance of normoglycemia was performed by surgical implantation, beneath the left renal capsule, of 650 syngeneic islets freshly isolated from young (5 to 7 weeks of age) prediabetic NOD females. The exogenous islets were removed by unilateral nephrectomy.

The glucose concentration of orbital blood from non-fasted animals was monitored two to three times a week after transplantation with a Glucometer Elite instrument (Bayer, Mishawaka, Ind.), and transplantation was considered successful if the glucose concentration was reduced to <150 mg/dL within 24 hours after surgery. Body weight was also monitored two to three times a week. Islet grafts were considered to have been rejected if the blood glucose concentration had increased to >250 mg/dL on two consecutive occasions.

Flow cytometry. Spleens were gently minced on a stainless steel sieve and the resulting spleen cell suspensions as well as heparinized blood collected from the orbital vein were rendered free of red blood cells by a 5-min. exposure to a solution containing 0.83% $NH_4Cl$. Lymphocytes were then stained with phycoerythrin-conjugated mouse monoclonal antibodies to $H-2K^b$ and with FITC-conjugated mouse monoclonal antibodies to $H-2K^d$ (Becton-Dickinson, San Diego, Calif.), after which they (>10,000 cells per sample) were subjected to flow cytometry with a FACScan instrument (Becton-Dickinson).

Histology and immunofluorescence staining. NOD mice were sacrificed by cervical dislocation and the pancreata were immediately removed and fixed for preparation of paraffin-embedded or cryopreserved sections. Serial sections of from 5 μm to 15 μm were fixed with formalin (10%) for 1 hour for hematoxylin-eosin staining, or with acetone (100%) for 10 min. at 4° C. for immunofluorescence analysis, and were then washed three times with phosphate-buffered saline (PBS). After incubation for 30 minutes with 5% mouse serum in PBS to prevent nonspecific binding of antibodies, the sections were stained for 2 hours with a rat monoclonal antibody to mouse CD45 (1:25 dilution) (NeoMarkers, Fremont, Calif.) or with polyclonal guinea pig antibodies to insulin (1:100) (Linco, St. Charles, Md.) or polyclonal rabbit antibody to anti-GFP (1:50) (Abcan Limited, Cambridge, UK); the antibody to CD45 reacts with all murine isoforms and allelic variants of CD45. The slides were then washed three times for 5 min. with PBS, incubated for 1 hour with FITC- or Texas red-conjugated goat secondary antibodies (Jackson ImmunoResearch Laboratories, West Grove, Pa.), and then washed again three times for 5 min. with PBS. Coverslips were applied with Vectashield mounting medium (Vector, Burlingame, Calif.) and the slides were examined with a fluorescence microscope. All fluorescence was evaluated both with a match and irrelevant filter to the label to prove the specificity of the signal.

FISH and confocal microscopic analysis. Single- and double-label fluorescence in situ hybridization (FISH) analyses were performed as described (Schwartz et al., *J. Clin. Invest.* 109: 1291-302; 2002). Whole organs, including the pancreas, brain, liver, and kidney, were immersed in OCT compound and then frozen at –80° C. Serial frozen sections (thickness, 5 μm) were cut, fixed with a mixture of methanol and acetic acid (3:1, vol/vol) for 90 min., dried in air, and dehydrated by exposure to a graded series of ethanol solutions. They were again dried in air, incubated in 70% formamide at 65° C. for 90 s. to 120 s., exposed to ice-cold 70% ethanol, and dehydrated with the graded series of ethanol solutions.

Nucleotide probes were individually denatured by incubation at 65° C. for 10 min. and then at 37° C. for 60 min. to 90 min. One (15 μL) or two (30 μL) probes were added to each slide, which was then covered with a 22 by 32 mm coverslip and sealed with frame fixative (Eppendorf, Westbury, N.Y.). After hybridization overnight at 42° C., the coverslip was removed, and, for detection of the Y chromosome alone, the biotin-conjugated probe (Cambio, Cambridge, UK) was visualized with Texas red-conjugated streptavidin. For detection of both Y and X chromosomes within the same nucleus, the corresponding probes were linked to FITC and Cy3, respectively. Nuclei were also stained with DAPI.

FISH analysis yields an undercount of Y chromosome-positive nuclei as a result of partial nuclear sampling in tissue sections. Although the thin tissue sections used for this analysis prevent false positives due to overlapping nuclear signals, they result in some nuclei (20%) in control male tissue sections being devoid of a detectable Y chromosome. The data shown in Table 2 for the percentages of Y chromosome-positive cells have thus been normalized by a correction factor of 0.8.

Confocal microscopy was performed with a Radiance 2100 instrument equipped with a Multi-Photon system (Bio-Rad, Hercules, Calif.). Fluorescence was excited at 488 nm and emission was monitored at >515 nm. Nuclear size was assessed by NIH image software (version 1.62).

RT-PCR and Western analysis. Polyadenylated RNA was isolated from the pancreas or spleen (including the capsule and trabeculae) of C57BL/6, CByB6F1, NOD, or NOD/LtSz-Prkdc$^{scid}$ (NOD SCID) mice. The latter animals are deficient in B and T cells and exhibit severe combined immune deficiency, with their pancreata thus devoid of insulitis and their spleens lacking most lymphoid cell populations. Complementary DNA synthesized from the isolated RNA by RT was subjected to PCR with primers specific for Pdx1 (CA-CAAGCTTGCGGCCACACAGCTCTAC (SEQ ID NO: 1); GAGGGATCCACACTCTGGGTCCCAGAC (SEQ ID NO: 2)), Hox11 (AAG-AAGAAGCCGCGCACATC (SEQ ID NO: 3); GGAGTCGTCAGACCACGGCT (SEQ ID NO: 4)) and beta-actin-1 (TAAAACGCAGCTCAGTAACAGTCGG (SEQ ID NO: 5); TGCAATCCTGTGGCATCCATGAAAC (SEQ ID NO: 6)). One step RT-PCR was performed on spleens and pancreata that were removed and soaked in RNA stabilization reagent (Qiagen Inc., Valencia, Calif.) overnight prior to total RNA extraction using an RNA isolation column (Qiagen Inc., Valencia, Calif.). The template of RNA was fixed at 2 μg for each sample and the reaction mixture was 12.5 mM $MgCl_2$, 10 mM of each deoxynucleoside triphosphate, 20 mM Tris-Cl (pH 8.7), 7.5 mM $(NH_4)_2SO_4$, 0.6 μg of each primer, 0.4 μL of RNase inhibitor (Invitrogen, Carlsbad, Calif.) and 2 μL of enzyme mix including reverse transcriptase and DNA polymerase. The amplification protocol comprised initial incubations of 50° C. for 30 min. and then 95° C. for 15 min.; 3 cycles of 94° C. for 1 min., 60° C. for 1 min. (Pdx-1) or 63.9° C. for 1 min. (Hox11) or 66.5° C. for 1 min. (beta-Actin) and 72° C. for 10 min. PCR products were separated by electrophoresis on a 1% Tri/Boric Acid/EDTA (TBE) agarose gel and stained with ethidium bromide.

For detection of GFP proteins in cytoplasmic pancreatic extracts, whole pancreases were placed in liquid nitrogen and then dissolved in 700 μL of phosphate buffered saline (pH 7.4) containing 100 μl, of protease inhibitor cocktail (protease inhibitor cocktail III; Calbiochem, San Diego, Calif.), 100 μL of phosphatase inhibitor cocktail 1 and 100 μL of phosphatase inhibitor cocktail 2 (Sigma, St. Louis, Mo.). Lysates were centrifuged for 3 min. at 500×g, and resulting supernatants were used. A total of 2 μg or 5 μg of protein per lane were separated by SDS-PAGE, and transferred onto nitrocellulose membranes. Positive GFP bands detected with anti-GFP antibodies were identified using ECL reagents (Amersham Bioscience, Piscataway, N.J.).

EXAMPLE 1

The Ability of Live Versus Irradiated Donor Splenocytes to Modulate Autoimmunity The ability of live versus irradiated donor splenocytes to modulate autoimmunity through selection of naïve T cells was examined as follows. Seventeen severely diabetic NOD females were randomized into two treatment groups that received CFA and either live or irradiated male CByB6F1 mouse splenocytes. This end-stage diabetic state was chosen to ensure both the lack of visible islets, either granulated or nongranulated, and the near-complete elimination of any remaining insulitis that might obscure dead or dying islets, as the pancreata of NOD mice with diabetes of recent onset may still contain scattered islets as well as remaining regions of insulitis (Table 1). Control of blood glucose concentration was achieved with a temporary implant of syngeneic islets under the capsule of one kidney. After the 40-day treatment regimen, the islet transplants were removed by unilateral nephrectomy and blood glucose concentrations were monitored to assess the recovery of endogenous pancreatic islets. Six of the nine NOD mice that received live splenocytes remained normoglycemic (FIG. 1A). In contrast, none of the eight NOD mice that received irradiated splenocytes remained normoglycemia and rapidly developed severe hyperglycemia after removal of the islet implants.

The ability of live or irradiated splenocytes to eliminate invasive insulitis, a sign of active autoimmunity, was assessed by examining the pancreatic histology of the treated animals. The pancreata of NOD mice with restored normoglycemia due to the injection of live splenocytes were removed ~80 days after the onset of therapy (~40 days after removal of the islet graft); that of NOD mice treated with irradiated splenocytes were removed after the return of hyperglycemia (~40 to 45 days after therapy initiation). Consistent with previous observations (Ryu, et al., *J. Clin. Invest.* 108: 63; 2001), the pancreata of normoglycemic animals treated with live splenocytes contained abundant islets almost uniformly devoid of invasive insulitis (FIG. 1B), with occasional islets associated with small, circumferentially distributed, regions of insulitis (peri-insulitis), a pattern associated with disease non-progression. The pancreata of NOD mice that received irradiated splenocytes also contained islets largely devoid of invasive insulitis, although the number of islets was smaller than that apparent in the animals treated with live splenocytes (FIG. 1B); these islets typically exhibited marked peri-insulitis, as confirmed by immunofluorescence staining with antibodies to CD45 (FIG. 1B), which selectively recognizes all lymphoid (not parenchymal) cells. These histological findings contrast with those observed in a 25-week-old prediabetic NOD mouse that had exhibited an increase (within 2 days) in blood sugar level to 250 mg/dL and whose pancreas exhibited an overall decrease in islet abundance, as well as invasive and peri-insulitis, that obliterated existing islet structure (FIG. 1B). Thus, when examined 40 to 45 days after the initiation of treatment, both live and irradiated splenocytes appeared able to reverse invasive insulitis, with live cells more effective in restoring normoglycemia, as well as inducing the reappearance of abundant pancreatic islets.

TABLE 1

Pancreatic islet histology of untreated NOD female mice.

| | | Islets | | |
|---|---|---|---|---|
| Age (weeks) | Blood glucose (mg/dL) | No. | Percentage granulated | No. of insulitis clusters* |
| 8 | 115 | 75 | 100 | 154 |
| 12 | 122 | 62 | 100 | 143 |
| 18 | 255 (1×)** | 9 | 15 | 54 |
| 25 | >400 (>2×)* | 1 | 0 | 3 |

*The number of islets counted are overestimates of the actual value because large islets that span adjacent sections are counted more than once. Insulitis clusters were defined either as islets with invasive insulitis or insulitis clusters without visible islet tissue.
**(1×) means this NOD mouse had one blood sugar at 255 at the time of sacrifice: (>2×) means this NOD mouse had two blood sugars greater than 400 mg/dL.

EXAMPLE 2

Kinetics of Pancreatic Islet Recovery

The kinetics of pancreatic islet recovery in additional groups of diabetic NOD mice was examined as follows. Twenty-five new and severely diabetic NOD females were randomized to treatment groups receiving CFA and either live or irradiated male splenocytes and temporary syngeneic islet transplants were maintained for 120 days before nephrectomy to allow a longer period for islet regeneration in situ. Eleven (92%) of the 12 NOD mice that received live splenocytes remained normoglycemic for greater than 26 weeks after disease onset or beyond 52 weeks of age. Moreover, 11 (85%) of the 13 NOD mice that received irradiated splenocytes also remained normoglycemic for greater than 27 weeks after disease onset or beyond 48 weeks of age (FIG. 1A). The longer period of ectopically imposed normoglycemia during treatment greatly increased the frequency of functional islet recovery in both experimental groups, with both live and irradiated splenocytes thus able to contribute to prolonged disease elimination. The average experimental landmark ages are provided in Table 2 for those mice that remained normoglycemic.

TABLE 2

Age at various experimental landmarks of NOD female restored normoglycemia*

| | Age (weeks) | |
|---|---|---|
| | Live splenocytes (n = 11) | Irradiated splenocytes (n = 11) |
| Diabetes and treatment onset | 26 ± 7 | 22 ± 6 |
| Treatment termination | 31 ± 6 | 28 ± 5 |
| Nephrectomy | 43 ± 3 | 39 ± 2 |
| Analysis of peripheral blood | 43 ± 7 | 39 ± 6 |
| Tissue analysis | 52 ± 7 | 48 ± 6 |

*Data are means ± SE.

The pancreatic histology of mice that had been successfully treated with live or irradiated splenocytes and had experienced persistent normoglycemia for ~9 weeks after nephrectomy was also examined (Table 3). The pancreata of the NOD mice that received irradiated splenocytes manifested the reappearance of pancreatic islets without invasive insulitis but with pronounced peri-insulitis, as revealed by hematoxylin-eosin staining. In contrast, the pancreata of NOD mice that received live splenocytes exhibited the reappearance of pancreatic islets without invasive insulitis and with minimal or no peri-insulitis (FIG. 1C, Table 3).

TABLE 3

Pancreatic islet histology of successfully treated NOD mice.
Pattern of insulitis (%)

| Animal | Splenocyte treatment | Invasive | Peri | None | Insulitis magnitude |
|---|---|---|---|---|---|
| #744 | Live | 2 | 11 | 87 | + |
| #788 | Live | 0 | 28 | 72 | ++ |
| #789 | Live | 0 | 15 | 85 | + |
| #790 | Live | 0 | 22 | 78 | + |
| #838 | Live | 0 | 31 | 69 | + |
| #699 | Irradiated | 43 | 57 | 0 | +++ |
| #703 | Irradiated | 2 | 87 | 11 | +++ |

Figure 2:
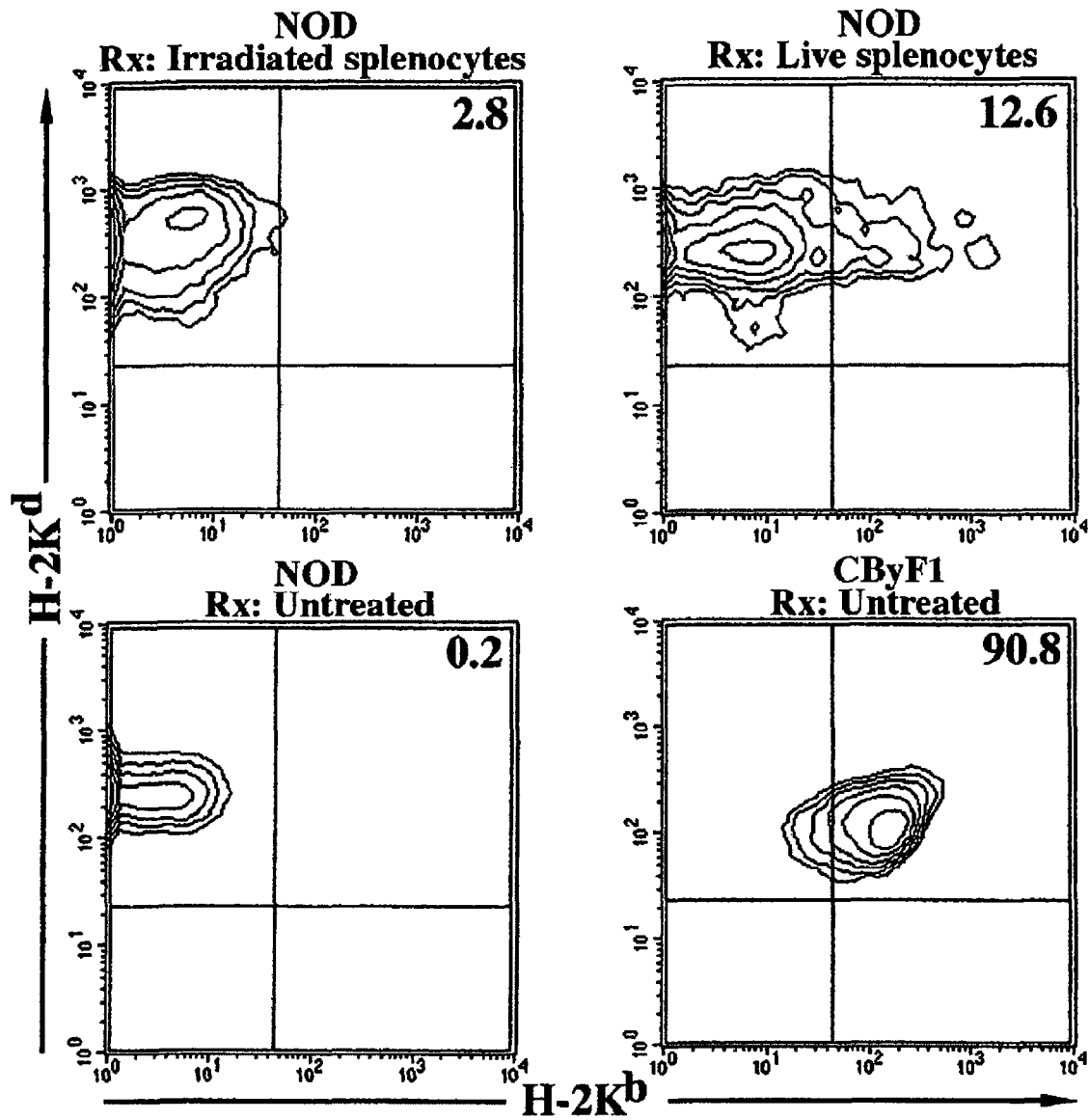
FIG. 2. shows a two-color flow cytometric analysis with antibodies specific for $H-2K^d$ or $H-2K^b$ on PBLs obtained from female NOD mice successfully treated with CFA and either live splenocytes (upper right panel) or irradiated splenocytes (upper left panel) from CByB6F1 males. Subrenal islet transplants were removed after 120 days and blood was collected 12 and 11 weeks after treatment termination, respectively. PBLs from an untreated NOD mouse at 12 weeks of age (lower left panel) and from a normal CByB6F1 mouse at 12 weeks of age (lower right panel) were similarly analyzed for comparison. The percentages of cells expressing both $H-2K^d$ and $H-2K^b$ are indicated.

The PBLs from NOD mice (H-2K$^d$) with disease reversal were examined for remaining live CByB6F1 donor cells (H-2K$^b$K$^d$) with allele-specific antibodies to the H-2K$^b$ or H-2K$^d$ MHC class I proteins. The results for five animals that received live splenocytes are shown in Table 4, and representative histograms for mice that received live or irradiated splenocytes are presented in FIG. 2. The PBLs from NOD mice treated with irradiated CByB6F1 splenocytes showed only background staining for H-2K$^b$, indicating that no donor hematopoetic cells remain. In contrast, 4.4% to 12.6% of the PBLs from NOD mice treated with live CByB6F1 splenocytes were of donor origin. PBLs from an untreated NOD mouse contained only cells expressing H-2K$^d$, and those from a CByB6F1 mouse contained exclusively cells coexpressing H-2K$^b$ and H-2K$^d$. NOD mice treated with live splenocytes thus exhibited a persistent low level of blood chimerism with semiallogeneic cells that was achieved without continuous immunosuppression or lethal preconditioning.

TABLE 4

Frequency and extent of donor engraftment in five NOD female mice with disease reversal.

| NOD Mouse No. | Age (weeks) | Lymphoid system | | Islets | | Pancreatic ducts | | |
|---|---|---|---|---|---|---|---|---|
| | | Donor PBLs (%) | Donor splenocytes (%) | Positive for donor cells (%) | Donor composition (%) | Donor pancreatic exocrine cells (%) | Positive for donor cells (%) | Donor composition (%) |
| #744 | 57 | 4.4 | 3.5 | 100 | 29 | 2 | 33 | 9 |
| #788 | 46 | 5.8 | 4.7 | 100 | 41 | 1 | 66 | 15 |
| #789 | 47 | 12.6 | 4.0 | 100 | 79 | 2 | 75 | 41 |
| #790 | 47 | 8.3 | 3.5 | 100 | 37 | 3 | 50 | 35 |
| #838 | 39 | 10 | 3.9 | 100 | 46 | 2 | 50 | 11 |
| Control NOD female | 38 | 0.3 | 0.3 | 3 | 2 | 2 | 1 | 1 |

TABLE 3-continued

Pancreatic islet histology of successfully treated NOD mice.
Pattern of insulitis (%)

| Animal | Splenocyte treatment | Invasive | Peri | None | Insulitis magnitude |
|---|---|---|---|---|---|
| #745 | Irradiated | 21 | 58 | 21 | +++ |
| #752 | Irradiated | 44 | 56 | 0 | ++ |
| #754 | Irradiated | 25 | 75 | 1 | +++ |

*Approximately 10 islets were examined for each NOD recipient and the dominant pattern of insulitis was determined for each islet; the predominant extent of insulitis (+, ++, or +++) among the islets of each pancreas is also presented.

EXAMPLE 3

Hematopoetic Chimerism

Lethal preconditioning (such as whole-body irradiation) of a host and introduction of MHC-matched bone marrow cells results in long-term hematopoetic chimerism (Weissman, Science 287: 1442, 2000). To determine whether hematopoetic chimerism also occurred in the non-preconditioned NOD mouse hosts that received live or irradiated splenocytes according to the treatment protocol of Example 4, the peripheral blood lymphocytes (PBLs) of these animals was examined by flow cytometry at mean ages of 43 and 39 weeks, respectively, ~17 weeks after diabetes onset and >11 weeks after the last injection of donor splenocytes (Table 2). Blood was obtained from the orbital vein, thereby allowing the mice to live after its collection.

EXAMPLE 4

The Contribution of Exogenous Splenocytes to Islet Regeneration

The possibility that live injected CByB6F1 male splenocytes contribute to both diverse lymphoid cells and nonhematopoetic tissues, such as the newly appearing islets in the pancreas of successfully treated NOD females, was investigated. At 39 to 57 weeks of age, NOD mice with stable disease reversal induced by CFA and live CByB6F1 splenocytes were sacrificed for further analysis of hematopoetic and parenchymal chimerism.

Among the splenocytes from the five successfully treated NOD mice examined, flow cytometric analysis revealed the presence of from 3.5% to 4.7% of cells positive for both H-2K$^d$ and H-2K$^b$, compared to a background level of 0.3% double-positive staining for splenocytes from an untreated control NOD mouse, confirming the persistence of donor CByB6F1 cells in all recipients. Differential gating for markers of various hematopoetic lineages revealed that CByB6F1 donor splenocytes contributed to T cells (CD3$^+$), monocytes (Mac1$^+$), and B cells (CD45R$^+$).

Parenchymal tissues were then examined for chimerism by FISH analysis for detection of the Y chromosome of the male donor cells. Serial sections of the pancreas were first evaluated for the presence of islets both by hematoxylin-eosin staining and by immunofluorescence analysis with antibodies to insulin and large well-formed islets were identified by both methods in the five successfully treated NOD mice examined.

Figure 3:
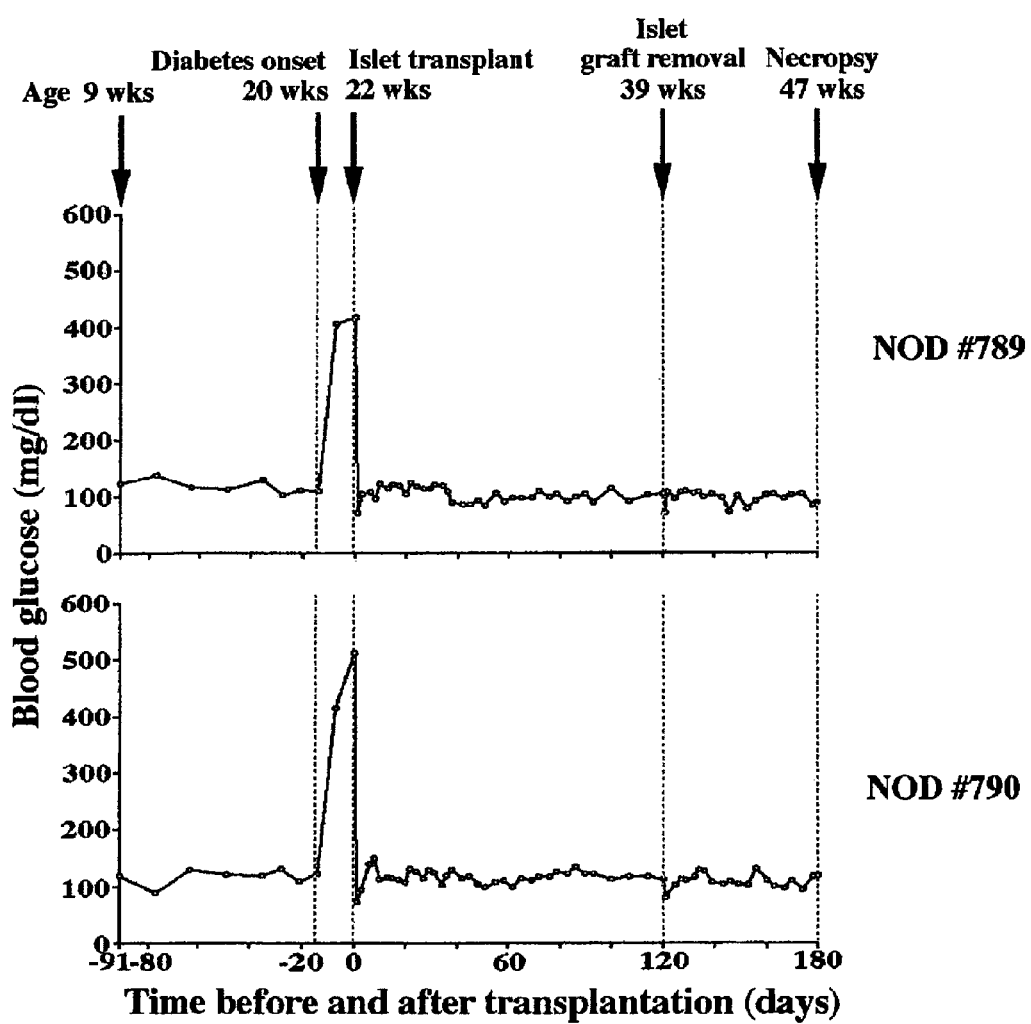
FIG. 3. shows long-term restoration of normoglycemia and the direct contribution of donor splenocytes to islet regeneration in successfully treated NOD female mice. (A) Blood glucose concentrations during the lifetime of two NOD females (#789 and #790 in Table 2) successfully treated with CFA and CByB6F1 male splenocytes as well as with a temporary subrenal transplant of syngeneic islets. (B) Immunofluorescence and fluorescence in situ hybridization (FISH) analyses of serial pancreatic sections from the successfully treated NOD females #789 (left panels) and #790 (right panels). The two top panels show immunofluorescence staining of islets with antibodies to insulin (red); the subsequent three pairs of images show FISH signals obtained with a Y chromosome-specific probe (pink dots) and nuclear staining with DAPI (blue) in sections containing islets (arrows), pancreatic ducts (arrowheads), and exocrine pancreas, respectively. (C) Immunofluorescence and FISH analyses of serial pancreatic sections from a C57BL/6 male (left panels) and C57BL/6 female (right panels). The two top panels show immunofluorescence staining of islets with antibodies to insulin (red); the subsequent three pairs of images show FISH signals obtained with a Y chromosome-specific probe (pink dots) and nuclear staining with DAPI (blue) in sections of the endocrine and exocrine portions of the pancreas as in (B). (D) Representative confocal micrographs obtained from three focal planes (−3, 0, and +3 μm) of a pancreatic section derived from the successfully treated NOD mouse #789. Images show staining with antibodies to insulin (green) and nuclear staining (red) for a large islet surrounded by exocrine tissue. The lower panels are higher magnification views of the fields shown in the upper panels.
Figure 3:
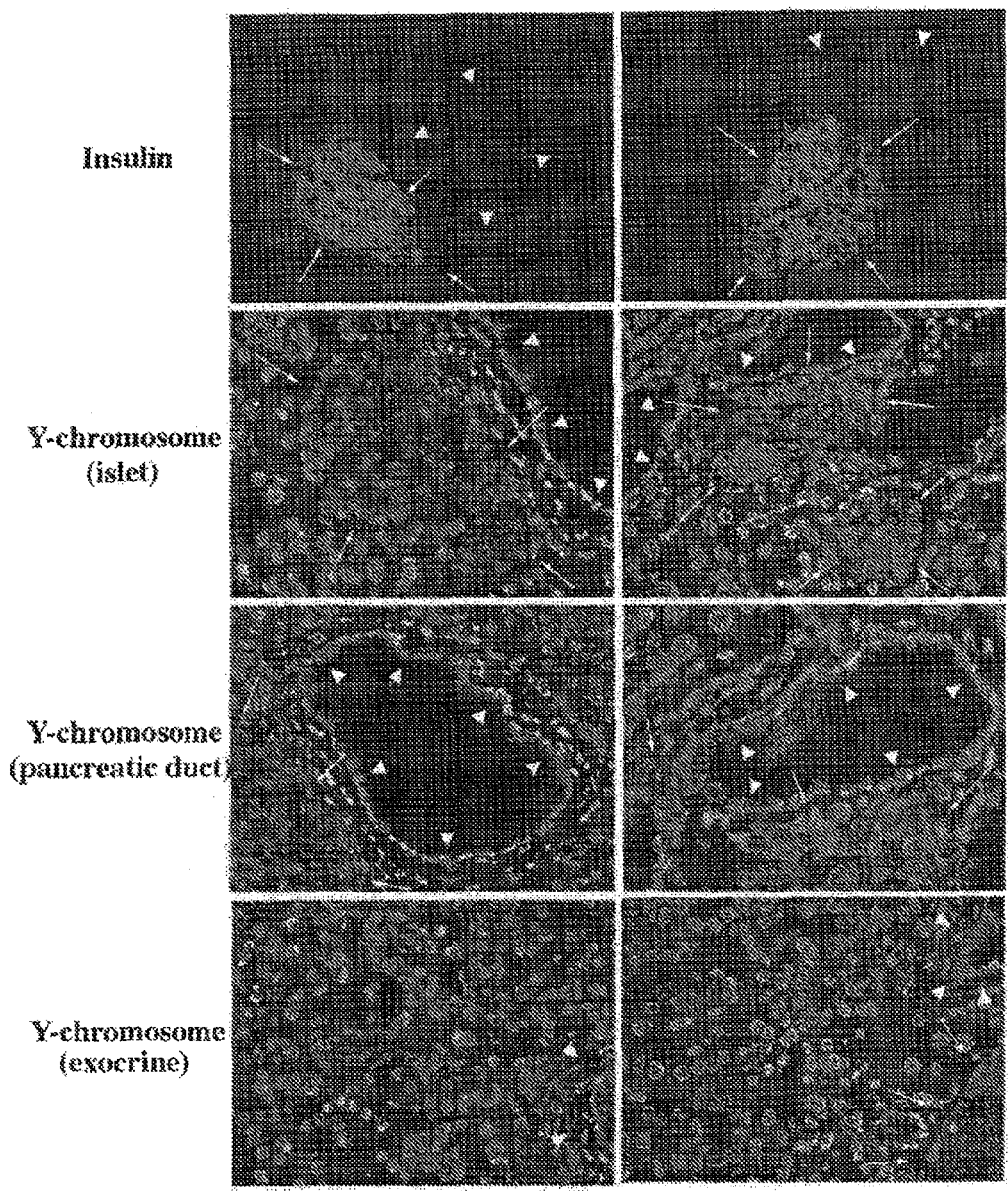
Figure 3:
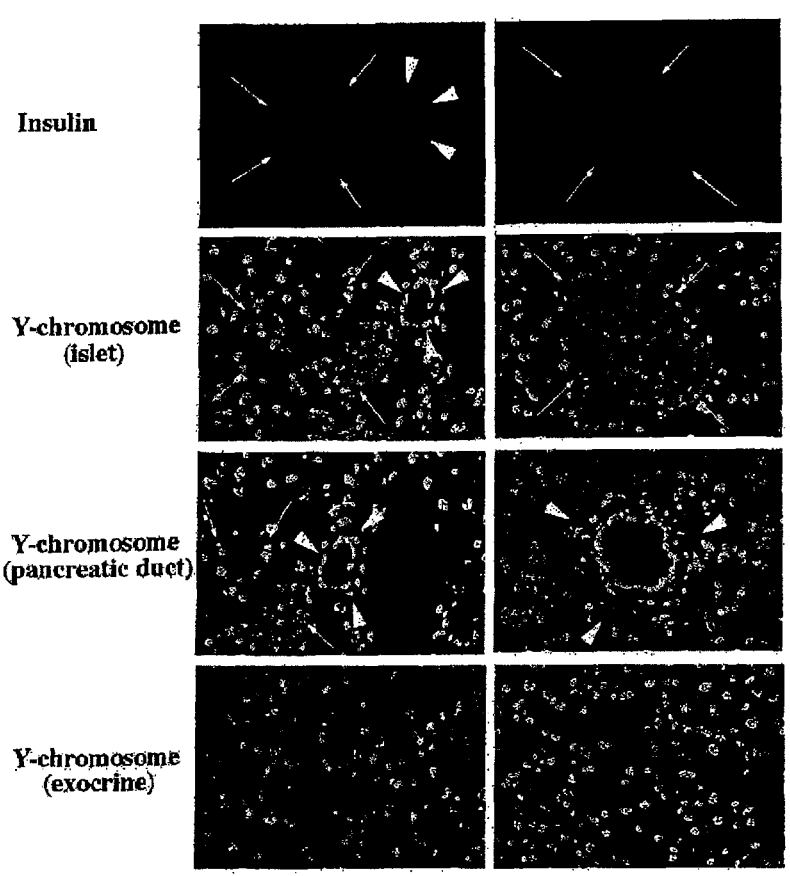
Figure 3:
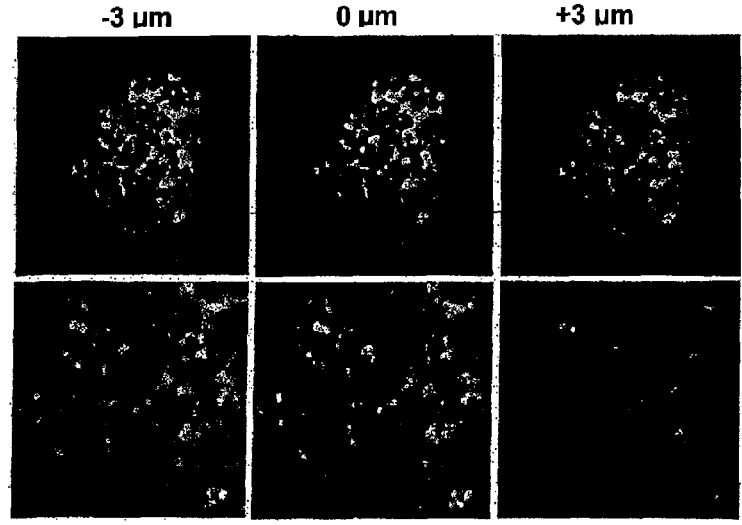

Data for two animals are shown in FIG. 3A and FIG. 3B. Blood glucose measurements demonstrated that therapy restored long-term normoglycemia until the mice were sacrificed at 47 weeks of age FIG. 3A. Staining of serial pancreatic sections with antibodies to insulin revealed a homogeneous insulin content in the large islets FIG. 3B, consistent with the restored normoglycemia. Single-color FISH analysis revealed the presence of abundant nuclei positive for the Y chromosome within the islets, as defined by morphology and insulin immunoreactivity FIG. 3B. In contrast, the exocrine portions of the pancreas were largely devoid of male cells. Similar results were obtained with all five treated NOD female mice examined. Quantitative analysis revealed that 29% to 79% of islet cells in these five animals were of donor origin. No islets solely of host origin were detected, consistent with the fact that the pancreas of NOD females before treatment lacks detectable islets as well as remaining clusters of insulitis.

Male donor cells also contributed to the epithelium of NOD female pancreatic ducts, although the distribution of male cells in this tissue was more heterogeneous than that found in the islets FIG. 3B. Among the five treated NOD females studied in detail, 33% to 75% of the ducts contained genetic material of male origin. Ducts purely of host origin were never associated with an adjacent islet containing male cells. The proportion of male cells in the pancreatic ducts of the five NOD mice ranged from 9% to 41%. Single-color FISH analysis revealed the presence of abundant nuclei positive for Y chromosomes within both the exocrine and endocrine portions of the pancreas of control C57BL/6 male mice, whereas the pancreas of control C57BL/6 females was devoid of Y chromosomes FIG. 3C.

The possibility that intrapancreatic lymphocytes were responsible for the Y chromosome signals detected in islets or pancreatic ducts of treated NOD females was excluded. As already shown, the introduction of live donor splenocytes uniformly eliminated invasive insulitis throughout the pancreas of NOD mice, as revealed by hematoxylin-eosin staining of complete sets of serial pancreatic sections; with lymphoid cells only rarely observed within the islets (FIG. 1C, Table 3). Furthermore, FISH analysis of tissue sections derived from the liver, brain, skin, or kidney of successfully treated NOD mice demonstrated the virtual absence of parenchymal signals for the Y chromosome, rendering it unlikely that normal intraparenchymal lymphoid cells, or passenger lymphocytes, were responsible for the Y chromosome signals in islets and pancreatic ducts.

Some recent studies have attributed the observed plasticity of adult stem cells in vivo to fusion with embryonic stem cells during prior culture (Terada et al., Nature 416: 542, 2002; Ying et al., Nature 416: 545, 2002). The hybrid cells contain markedly enlarged nuclei and multiple nucleoli and are tetraploid. With the use of serial sections and confocal microscopy, >800 nuclei in β cells as well as >800 nuclei in adjacent exocrine tissue of the five treated NOD females was studied in detail. Data for one of these animals are shown in FIG. 3D and Table 5. At three scanning focal lengths, none of the regenerated cells within the islets was enlarged compared with the adjacent native exocrine cells. The β-cell nuclei were of normal size and did not contain multiple nucleoli. These observations suggest that the regenerated islet cells were not the products of fusion between donor splenocytes and endogenous dying or injured β cells.

TABLE 5

Comparison of nuclear diameter between β cells and exocrine cells in a successfully treated NOD mouse (#789 in Table 2).*

| Scanning position | β cells | | Exocrine cells | | |
|---|---|---|---|---|---|
| | Number | Nuclear diameter (pixels) | Number | Nuclear diameter (pixels) | P |
| −3 μm | 89 | 29.1 ± 4.0 | 91 | 36.0 ± 6.3 | 0.554 |
| 0 μm (standard) | 85 | 33.0 ± 4.3 | 91 | 36.8 ± 6.5 | 0.054 |
| +3 μm | 112 | 32.0 ± 5.8 | 102 | 33.8 ± 7.0 | 0.147 |

*Pancreatic sections stained with antibodies to insulin and propidium iodide were examined with a confocal microscope at three different focal planes. Nuclei in insulin-positive cells were counted as β-cell nuclei and those in insulin-negative cells in the exocrine portion of the pancreas were counted as exocrine cell nuclei. Nuclear diameter was determined by NIH Image software. Data are means ± SD for the indicated number of nuclei examined. The P values for comparisons between islet and exocrine cells were obtained by Student's t test.

Figure 4:
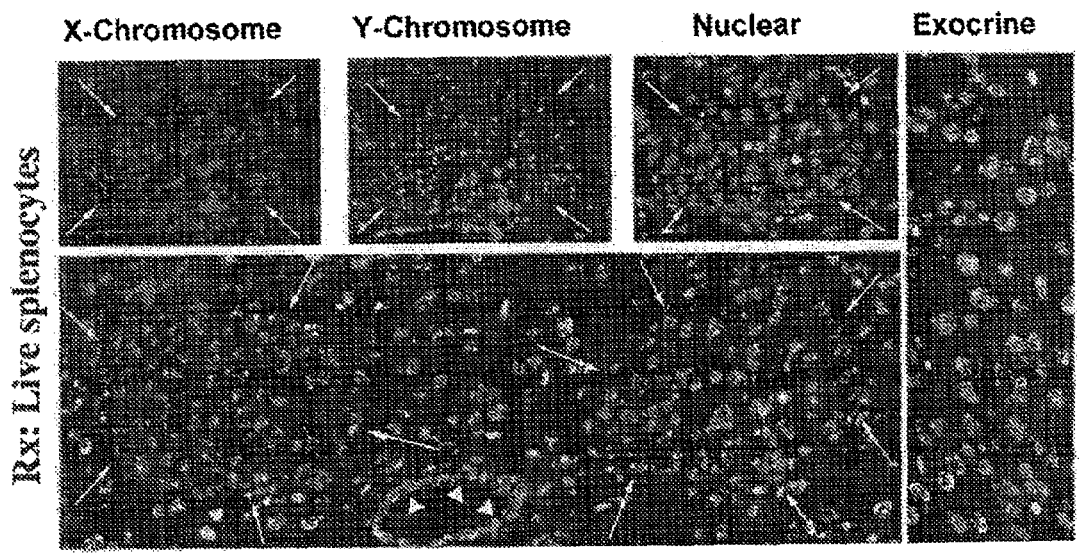
FIG. 4. shows two-color FISH analysis of the sex chromosomes of NOD female mice successfully treated with either live or irradiated male splenocytes. (A) Analysis of islet and pancreatic duct chimerism in NOD females successfully treated with live (top panels) or irradiated (bottom panels) CByB6F1 male splenocytes. Pancreatic sections were subjected to nuclear staining with DAPI (blue) and to FISH analysis with a Cy3-conjugated X chromosome-specific probe (red dots) and an FITC-conjugated Y chromosome-specific probe (green dots). Purple represents overlap of Cy3 and DAPI signals. Arrows indicate the outlines of islets (B) Control pancreatic sections from an untreated NOD female (left panel) and an untreated NOD male (right panel) stained as in (A). (C) Sections prepared from the brain, liver, and kidney of a NOD female mouse after long-term disease reversal induced by treatment with CFA and live CByB6F1 male splenocytes were stained as in (A).
Figure 4:
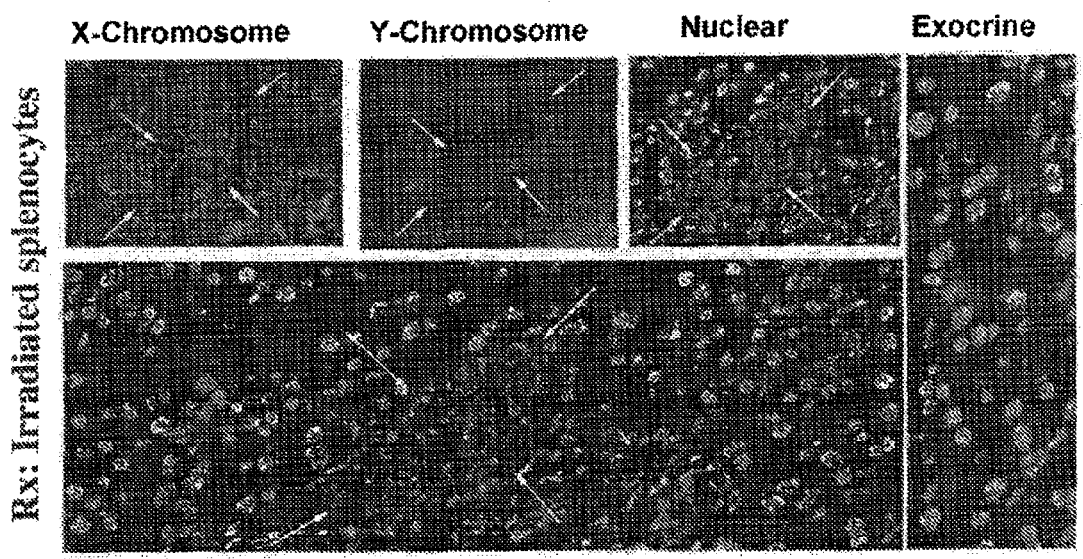
Figure 4:
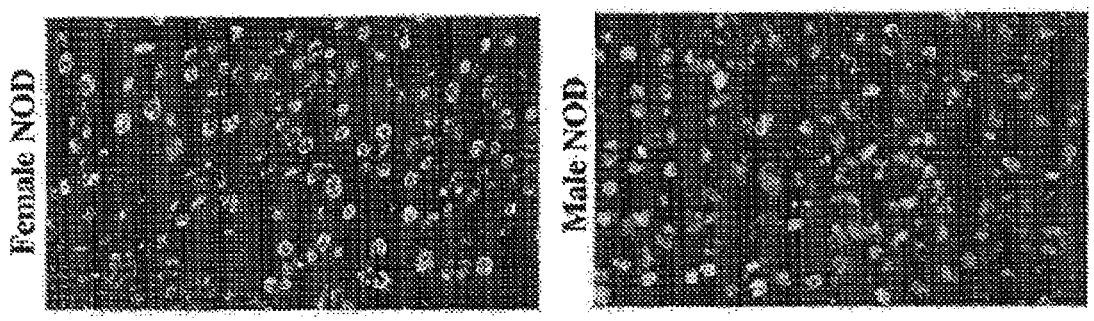
Figure 4:
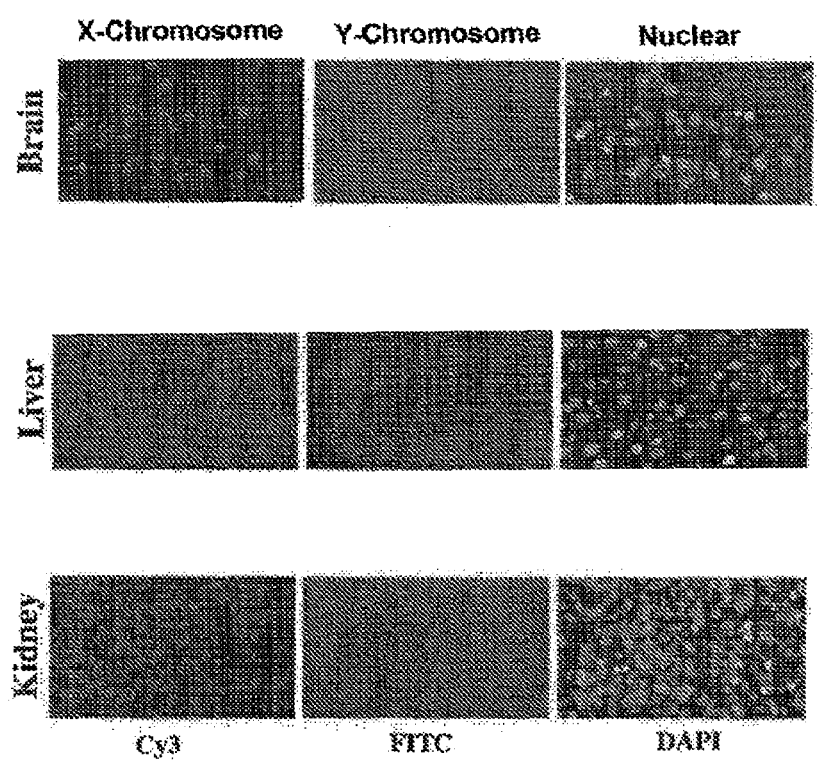

The ploidy of the sex chromosomes of cells in the regenerated islets of successfully treated NOD mice by two-color FISH analysis with a Y chromosome specific probe linked to fluorescein isothiocynate (FITC) (green) and an X chromosome-specific probe conjugated with Cyanine 3 (Cy3) (red) was further examined. Islet cell nuclei were also stained blue with 4',6-diamidino-2-phenylindole (DAPI). FIG. 4A shows islets predominantly of male origin in a NOD female successfully treated with live splenocytes from CByB6F1 males. Inspection of individual nuclei revealed only rare if any islet cells with an apparent XXY or XXXY genotype. A normal complement of sex chromosomes was also observed in the pancreatic duct epithelium. These results thus again indicate that the regenerated islet cells were unlikely the result of frequent fusion between donor male cells and host female cells.

Similarly, the regenerated islets of a NOD female with long-term disease reversal due to treatment with CFA and irradiated splenocytes from CByB6F1 males were also examined. None of the islet cell nuclei contained a detectable Y chromosome, with each nucleus yielding two red signals, corresponding to a genotype of XX (FIG. 4A). Two-color FISH analysis of the pancreas of untreated female and male NOD mice revealed that, although this methodology can yield false negative data (female nuclei with no red signal or only one red signal), it almost never yielded false positive data (a green signal in the nucleus of a female cell or two green signals within an individual male nucleus) (FIG. 4B).

EXAMPLE 5

The Analysis of Hox11 Expression

Figure 5:
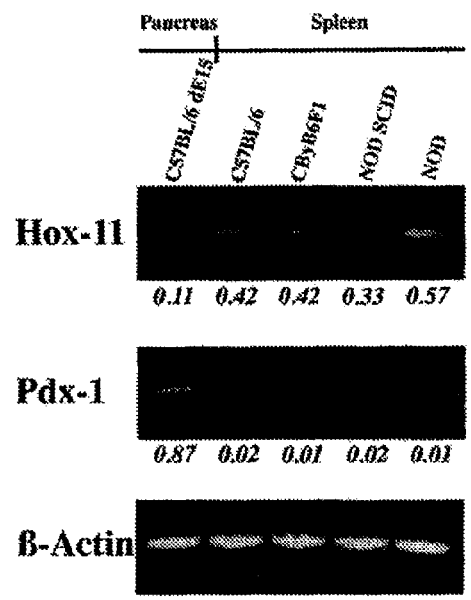
FIG. 5. shows the identification of Hox11-expressing pluripotent cells in the spleen of adult mice and the effect of treatment with separated $CD45^-$ or $CD45^+$ compared to whole CByB6F1-GFP splenocytes on pancreatic histology in prediabetic NOD mice. (A) Polyadenylated RNA isolated from the pancreas of a C57BL/6 mouse embryo at E15 or from the spleen of adult C57BL/6, CByB6F1, NOD SCID, or NOD mice was subjected to RT-PCR analysis with primers specific for Hox11, Pdx1, or the β-actin gene. The amounts of PCR products derived from Hox11 and Pdx1 mRNAs were determined by densitometry and normalized by the corresponding amount of that derived from β-actin mRNA; the normalized values are shown. (B) Western blot. Pancreatic extracts (2 μg or 5 μg) from control and treated NOD mice probed with anti-GFP antibodies. (C) Prediabetic NOD females (12 weeks old) were treated with CFA and $CD45^-$ (left upper panels) $CD45^+$ (right upper panels) or whole (left lower panels) CByB6F1-GFP splenocytes and were monitored for >120 days. Serial pancreatic sections containing islets identified with insulin and CD45 co-staining were then subjected to immunohistochemical analysis with an anti-GFP antibody (green). Right panels: Rhodamine filter. (D) Serial pancreatic sections from a diabetic NOD, prediabetic NOD (12 weeks old), C57BL/6 control, prediabetic NOD female treated with CFA and whole CByB6F1 splencoytes, prediabetic NOD female treated with CFA and CD45+ CByB6F1 splencoytes, and prediabetic NOD female treated with CFA and $CD45^-$ CByB6F1 splenocytes were subjected to immunofluorescence analysis with antibodies to insulin (red) or to CD45 (green), as indicated; merged images are shown in the bottom row.
Figure 5:
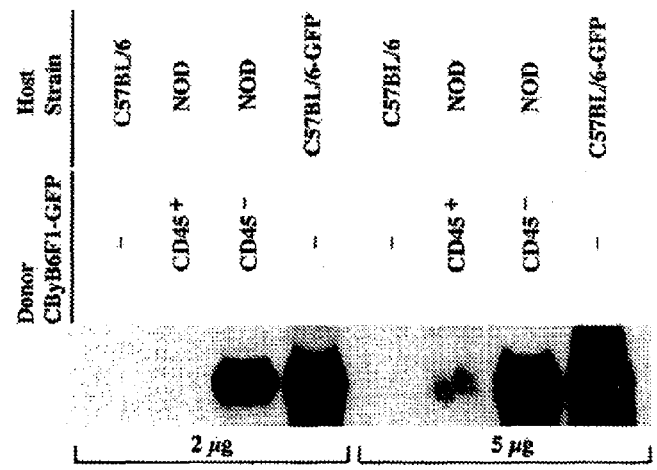
Figure 5:
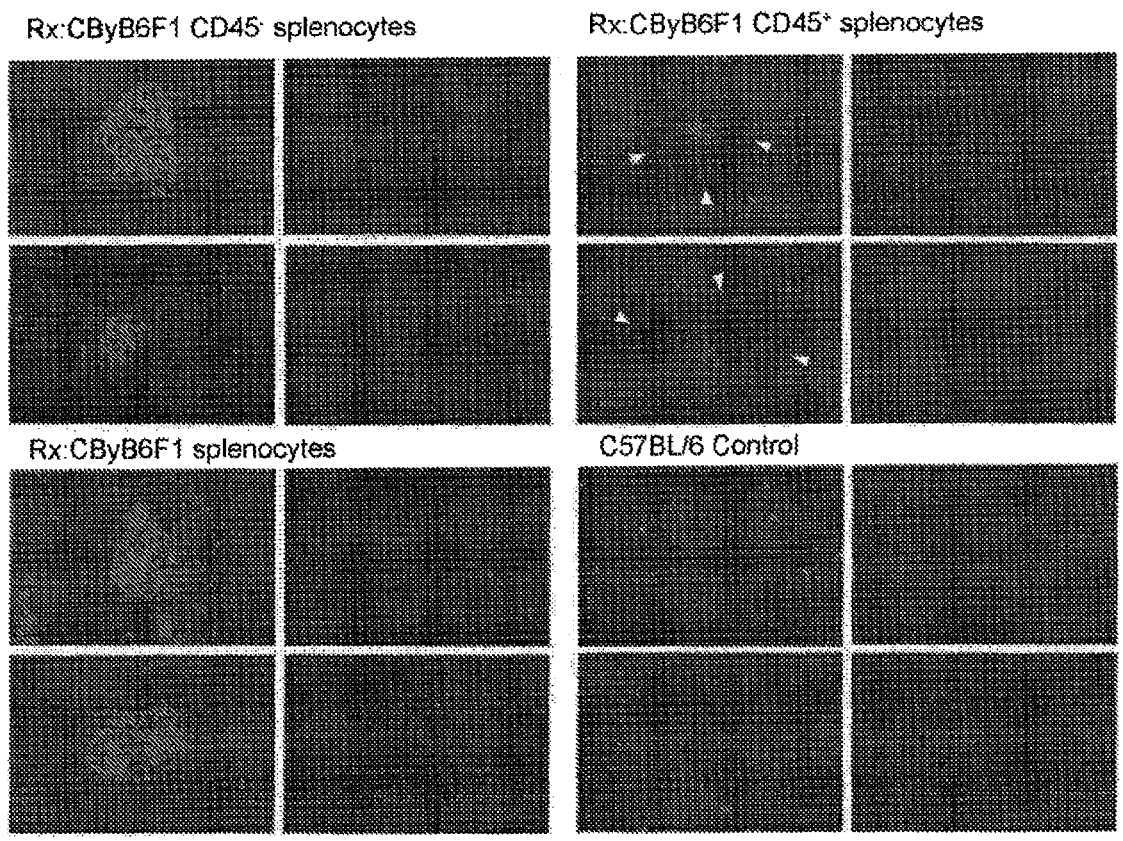
Figure 5:
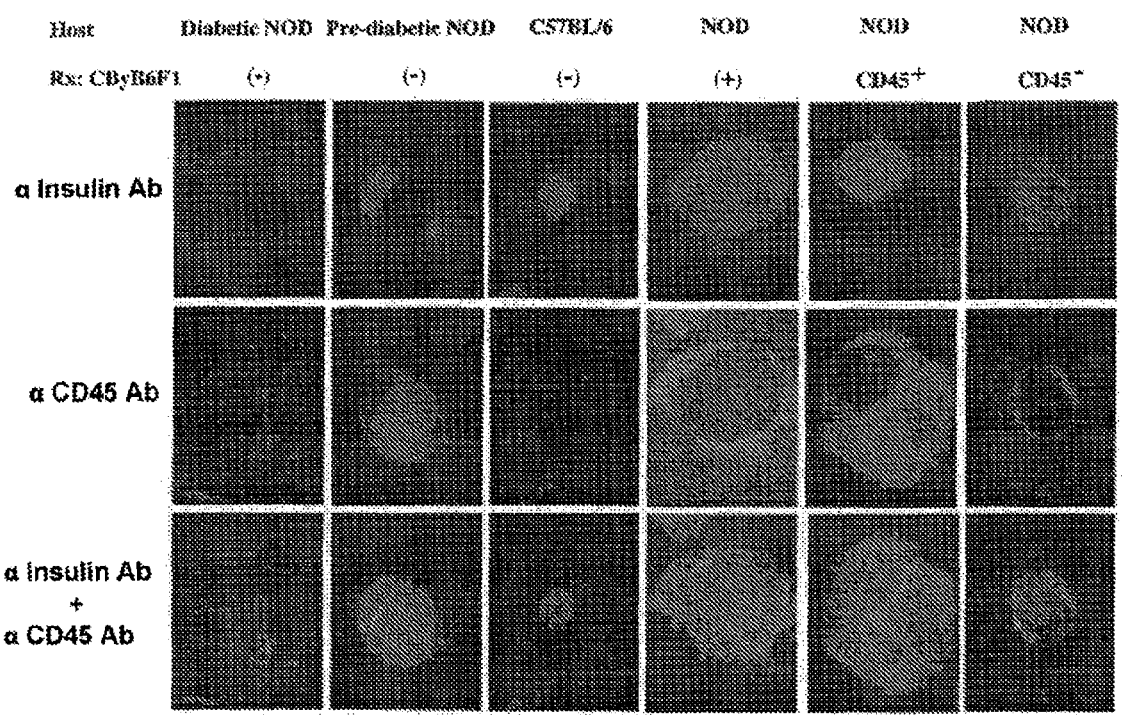

The spleens of adult C57BL/6, CByB6F1, NOD SCID, and NOD were examined by reverse transcription (RT) and polymerase chain reaction (PCR) analysis for Hox11 expression. The analyses revealed the presence of abundant Hox11 transcripts in the spleen of 12-week-old animals in each of the mouse strains examined (FIG. 5A). The presence of Hox11 mRNA in the spleen of NOD SCID mice, which lack most lymphoid cell populations, confirms that Hox11 is expressed in the nonlymphoid portions of the adult spleen. Pancreatic tissue from C57BL/6 embryos at embryonic day 15 (E15) did not contain Hox11 mRNA (FIG. 5A).

In addition, the spleens and pancreatic of adult mice were examined for the expression of the Pdx1 gene, which marks the dorsal and ventral pancreatic buds between E8.5 and E16.5 (Offield et al., Development 122: 983-95, 1996). It was found that the spleens of adult mice do not contain Pdx1 mRNA, whereas the pancreata of C57BL/6 embryos at E15 do (FIG. 5A). Together, these data indicate that a pluripotent cell that expresses Hox11, does not express the early pancreatic lineage marker Pdx1, and is not of lymphoid (CD45$^+$) origin is present in the spleen of adult mice.

EXAMPLE 6

The Use of CD45$^+$ Vs. CD45$^-$ Splenocytes

To examine the possible role of this non-lymphoid stem cell population in the regeneration of pancreatic islets in NOD mice treated with live donor splenocytes, 12-week-old NOD females (n=20) were injected with either CD45$^+$ or CD45$^-$ CByB6F1-GFP$^+$ splenocytes, as well as unseparated splenocytes. All groups of NOD mice also received CFA and blood glucose and were monitored for >120 days. These experiments differ from previous experiments in that the NOD females used were prediabetic (i.e., with residual islet function but with active autoimmunity at the start of treatment), did not receive an islet graft, and the number of splenocytes cells they received by injection was reduced to $4 \times 10^5$ to $5 \times 10^5$, administered four times over 2 weeks. GFP fluorescence was use as a monitoring method to document re-growth of the islet cells from the injected donor splenocytes. All of the NOD females that received CD45$^+$ CByB6F1-GFP$^+$ (n=5) or CD45$^-$ (n=5) CByB6F1-GFP$^+$, as well as those that received unseparated splenocytes (n=10) remained normoglycemic during the monitoring period, whereas all untreated NOD littermates (n=10) became diabetic under similar housing and observation conditions. The treated animals were subsequently sacrificed after 120 days of normoglycemia and the pancreas was subjected both to Western analysis for overall GFP+ expression (FIG. 5B) and serial pancreatic sections were subjected to immunohistochemical analysis for the detection of the individual fluorescence of CByB6F1-GFP$^+$ cells in pancreatic islets (FIG. 5C). Sections were also stained with antibodies to CD45 and to insulin (FIG. 5D).

Long term normoglycemic NOD mice with successful disease reversal secondary to a brief low dose treatment with either CD45$^+$ or CD45$^-$ splenocytes from CByB6F1-GFP mice showed opposing GFP protein expression in the pancreas. Pancreatic extracts of NOD mice treated over 120 days earlier with enriched populations of CD45$^-$ splenocytes showed a strong GFP protein expression, with NOD mice treated with CD45$^+$ splenocytes having an almost undetectable GFP signal (FIG. 5B). Cytoplasmic pancreatic extracts of CByB6F1-GFP mice showed a strong band reactive with anti-GFP antibody, with control C57BL/6 mice showing no GFP reactive band (FIG. 5B). Co-treatment of prediabetic mice with CByB6F1 CD45$^-$ splenocyte and CFA resulted in the persistence of pancreatic located cell populations expressing a stable long-term GFP+ derivative of the introduced splenocyte population.

Similar to the results obtained in Example 5 with severely diabetic NOD mice treated with live splenocytes, the pancreata of prediabetic NOD females treated with either CD45$^-$ CByB6F1-GFP or unseparated CByB6F1-GFP spleen cells contained islets positive for the GFP marker (FIG. 5C). Furthermore, the newly generated islets lacked invasive lymphocytes and were associated with minimal or no peri-insulitis, as observed with insulin and CD45 co-staining (FIG. 5D). The number of islets of GFP origins appeared less frequent in prediabetic NOD females treated with CD45$^-$ or whole splenocytes than in severely diabetic NOD females, consistent with the fact that the pancreata of prediabetic mice still contained endogenous islets affected by peri-insulitis and that the treatment of pre-diabetic animals with mobilized precursor cells thus rescued damaged islets and also promoted de novo islet regeneration.

The pancreas of prediabetic NOD females treated with CD45$^+$ splenocytes also contained islets free of invasive insulitis. Immunohistochemical analysis, however, revealed the absence of islets positive for the GFP marker in these female hosts (FIG. 5C). Furthermore, similar to the islet regeneration observed in severely diabetic NOD mice treated with irradiated splenocytes in Example 5, the newly appearing islets in prediabetic NOD females treated with CD45$^+$ splenocytes exhibited pronounced peri-insulitis (FIG. 5C and FIG. 5D).

EXAMPLE 7

CD180-Deficient Cells as a Target for the Treatment of Diabetes

CD180 (RP150) is a toll-like receptor (TLR) that is critical for the response of B cells to bacterial lipopolysaccharide (LPS). Whole NOD splenocytes from NOD mice greater than 12 weeks of age were analyzed by mass spectrometry for the presence of this protein. Lymphoid cells of B6 mice (normal control) were then separated into non-T-cell and T-cell populations, both of which were similarly analyzed by mass spectrometry. It was found that CD180 protein was detected in the non-T cell fraction of the control mice but not in the NOD mice. As expected, T cells from both NOD mice and B6 mice did not express CD180, as this protein is believed to be restricted to B cells.

It was then found that, in the diabetic mouse, BCG administration kills the subpopulation of B cells that are CD180-deficient. In one experiment, NOD and B6 mice were subjected to BCG treatment via one subcutaneous injection in the footpad. Two days after BCG treatment, the splenocytes were removed and examined for CD180 antigen, at which time both B6 and NOD mice showed equivalent amounts of CD180 antigen in the non-T cell populations. These results were confirmed with analysis by Western gels.

It is known that at least two TLRs expressed on mature B cells (TLR4 and CD180) mediate LPS signaling. The finding that a subpopulation of B cells involved in autoimmunity may be linked to defective CD180 expression and that this subpopulation of autoreactive B cells is eliminated with LPS, or other receptor agonists (such as, for example, those that bind to Toll, TLRs, MD-1, or Ly78) defines a novel way to interfere with autoreactivity in the B cell compartment, therefore identifying a novel therapy for autoimmune diseases (e.g., Type 1 diabetes) based on the selective killing of disease causing cells.

Agents that can affect the elimination of autoreactive B cells that are deficient in CD180 expression include, small molecule or antibody agonists of TLR1 (such as, for example, triacetylated lipopeptides (LP), phenol-soluble modulin, or OspA LP from *B. burgdorferi*), small molecule or antibody agonists of TLR2 (such as, for example, LP with TLR1 or TLR6, or HSP60 with TL4), small molecule or antibody agonists of TLR3 (such as, for example, double-stranded RNA), small molecule or antibody agonists of TLR4 (such as, for example, LPS from Gram-negative bacteria, HSP60, mannuronic acid polymers, flavolipins, tecihuronic acids, neumolysin, fimbriae, surfactant protein A, hyaluronan, oligosaccharides, heparin sulfate fragments, fibrinogen peptides, or beta-defensin-2), small molecule or antibody agonists of TLR5 (such as, for example, flagellin), small molecule or antibody agonists of TLR6 (such as, for example, deacetylated LP or phenol-soluble modulin), small molecule or antibody agonists of TLR7 (such as, for example, imidazolquinoline anti-virals), small molecule or antibody agonists of TL8 (such as, for example, imidazolquinoline) or small molecule or antibody agonists of TLR9 (such as, for example, bacterial DNA as CpG motifs).

EXAMPLE 8

Treatment of Patients with Compositions Enriched in Pluripotent Cells that Express Hox 11

While the therapies described herein are likely to be effective in treating pre-diabetics, i.e., patients diagnosed as progressing to type I diabetes, but who are not yet hyperglycemic, we note that the methods of the inventions also may be used to treat a mammal, for example, a human with type I diabetes or any other autoimmune disease. The ability to treat patients who already have hyperglycemia and therefore have significant or total islet destruction is a significant advantage of the current therapy.

In general, before treating a patient with a composition of Hox11-expressing pluripotent cells, one may optionally obtain blood from the patient to determine that the patient has two disease phenotypes. The first disease phenotype is an increase in the number of circulating CD45RA positive cells in the blood (also defined as alterations in the number of cells positive for CD95, CD62L, or other markers of naive or unstimulated cells). CD45, CD95, and CD62L are all cell surface antigens that can be monitored by flow cytometry and compared to age matched controls. We expect to see an abundance of these naïve or unstimulated cells in the peripheral blood of subjects with diabetes or any other autoimmune disease. The second phenotype is the presence of a subpopulation of lymphocytes with augmented sensitivity to cell death through apoptosis or necrosis. For example, subpopulations of cells may have augmented sensitivity to cell death caused by TNF-alpha, TCR receptor cross-linking agents, T-cell specific antibodies (e.g., αTCR or αCD3), or nonspecific stimulation with BCG. We may assay for the presence of such cells by isolating lymphocytes from these patients, treating them in vitro with TNF-alpha, and showing that the lymphocytes contain a subpopulation that undergoes apoptosis or necrosis when exposed to TNF-alpha, other cytokines, chemical reagents, or antibodies to select surface proteins. Desirably, control donor lymphocytes do not exhibit sensitivity to these agents. This phenotype is a result of lymphoid cells predominantly of pathogenic origin that have altered intercellular signaling pathways, alterations which result in a heightened death sensitivity. Elimination or conversion of all cells with this phenotype is desirable for the permanent reversal of autoimmunity. The penetrance of these defects is likely to be relatively high in diabetic or other autoimmune patients, with the first phenotype likely having a penetrance of over 95%, and the second phenotype likely having a penetrance of over 50% in type I diabetics.

Accordingly, before beginning to treat a subject with type I diabetes or any other autoimmune condition, we may determine from blood analysis alone whether the subject has either or both of these two phenotypes and, therefore, is amenable to therapy. To treat the first phenotype (i.e., an increase in the number of circulating CD45RA positive cells) tolerance to MHC class I and self-peptide may have to be re-established. We conclude from our results that the lack of functional MHC class I and self-peptide complexes causes the overabundance of naïve T-cells in the periphery or at least results in one of the phenotypes that causes this. So for treating this phenotype, we can administer blood or bone marrow that is a semi-allogeneic or fully-allogeneic match to the MHC class I and self-peptide complex. Furthermore, the blood or bone marrow derived cells, or even fibroblasts that have been immortalized, desirably may have normal MHC class I and self-peptide complex presentation; in other words, they should not come from diseased patients. Those phenotypes are easily monitored prior to treatment to determine the suitability of the donor cells in this therapy. For example, conformationally specific MHC class I and self-peptide antibodies may be used to show that the complexes are properly filled. In addition, we know that, in this aspect of the treatment, an increased number of matches to the HLA class I alleles of the host results in an increase in the duration of the reversal of the disease. Desirably, at least two, and desirably all four HLA class I alleles (e.g., the HLA A and HLA B alleles) from the donor cells are matched. Accordingly, these donor cells may be perfectly matched or they may be semi-allogeneic (i.e., with only partial matches on individual cells).

Treatment may involve intravenous biweekly infusions of $1 \times 10^7$ cells of any given donor of any given class I haplotype. It is desirable for the administered cells to be freshly isolated and not processed with preservatives or frozen. Cells that may be used in the methods of the invention may be obtained, for example, from a bloodbank. In addition, semi-allogeneic cells may be obtained from a close relative of the patient, such as a parent or a sibling. Furthermore, it would be advantageous to have the red blood cells eliminated from the preparations to decrease the volume of blood and lymphocytes administered. Alternatively, pluripotent cells (e.g., splenocytes, or those derived from cord blood or embryonic stem cells) can be transfected with a gene for Hox 11, or induced to express Hox 11, and the resulting cells used for treatment.

As an alternative to administering MHC class I and peptide, another agent that inactivates or kills naive T-cells can be administered. Exemplary agents include antibodies that bind and inactivate the T-cell receptor on naive T-cells or by binding and triggering the selective death of only pathologic cells. In some embodiments, the antibodies inhibit the activity of or naive T-cells by at least 2, 5, 10, or 15-fold more than they inhibit the activity of memory T-cells.

Simultaneously with the administration of donor cells, it is also desirable to induce endogenous TNF-alpha production either through stimulation with *Bacillus* Clamette-Guerin (BCG) or other immune adjuvants such as CFA, or by the direct administration of TNF-alpha. For example, one may administer BCG at least biweekly or, desirably, three times a week. Again, one skilled in the art can determine individually the dosing of the cells and TNF-alpha or BCG by analyzing a blood sample twice a week for evidence of the elimination of the phenotype of the pathogenic cell. For instance, to determine the correct dose of donor MHC class I expressing cells, we may look for the elimination of the abundant naïve cells in the peripheral blood and to determine the correct dose of TNF-alpha or BCG, we may look for the elimination of TNF-alpha in vitro sensitivity.

With regard to the second aspect of the therapy, TNF-alpha, BCG, or another nonspecific form of immune stimulation may promote the induction of endogenous TNF-alpha. For example, TNF-alpha may be administered intramuscularly, intravesicularly, or intravenously. Moreover, recombinant human TNF-alpha or new drugs such as a TNF receptor 2 agonist may be used. Such compounds have two effects, one is the elimination of apoptosis or death sensitive cells in the periphery which can be monitored, and the other is the promotion of endogenous beta cell regeneration, as well as possibly differentiation from the new donor blood. Exemplary doses of TNF-alpha that may be administered to a patient are approximately 40 µg/m² or 200 µg/m². Other exemplary doses include doses between 2×10⁶ and 5×10⁶ mg daily for two doses in one week. Patients with an autoimmune disease may tolerate higher doses of TNF-alpha and/or may require lower doses for treatment. As an alternative to TNF-alpha, tolerance can be gained by cross-linking the TCR or by non-specific vaccination through the same pathway (e.g., BCG vaccination). As an alternative to administering an inducer of lymphopenia (e.g., TNF-alpha) directly to a patient, the inducer of lymphopenia can be administered to blood obtained from the patient (e.g., blood obtained during electrophoresis), and the treated blood can be re-administered to the patient. For induces of lymphopenia with a short half-life (e.g., TNF-alpha) little, if any, functional compound remains in the blood that is re-introduced into the patient. Thus, this method should decrease the incidence or severity of any potential adverse, side-effects of the compound.

Any combination therapy described herein, e.g. a therapy which uses MHC class I expressing cells and TNF-alpha induction, may be administered until the disease is successfully treated. For example, this therapy may be continued for approximately 40 days; however, this time-period may readily be adjusted based on the observed phenotypes. Additionally, the dose of TNF-alpha can be adjusted based on the percentage of cells in blood samples from the patient that have increased sensitivity to TNF-alpha, indicating the amount of remaining autoimmune cells. In addition, in treating type I diabetes, it may be desirable that the patient maintains as close to normoglycemia as possible. The murine data have demonstrated that marked fluctuation in blood sugars hamper the normal regenerative potential of the pancreas. Therefore, these patients may be placed on an insulin pump for not only the exemplary 40 days of disease reversing therapy, but also for a 120 day period to optimize the regenerative process. The pancreas of long-term diabetics (i.e., ones having diabetes for more than 15 years) may have the regenerative potential of the pancreas diminished to such a degree that the precursor cells are no longer present. In these patients, the therapy may be identical except for the length of the treatment. For instance, the donor blood or bone marrow cells have to be alive for these cells to convert to the correct tissue type, such as into beta cells of the pancreas.

As is mentioned above, some embodiments of the invention employ pluripotent cells that express Hox 11, isolated from a normal donor (e.g., from the bone marrow, the spleen, or the peripheral blood, preferably from the spleen). Typically, this cell expresses, to a detectable degree, CD90⁺, CD44⁺, or CD29⁺, but does not express appreciable amounts of CD45 or CD34. This normal donor cell is administered to a person, preferably intravenously or intraperitoneally, to allow for rapid transport to the site of inflammation, injury, or disease. Desirably, this cell is administered to a person with active autoimmunity. Alternatively, the cell may be administered to a person without autoimmunity or to a person with quiescent autoimmunity. The absence of active autoimmunity in a person (host) may require pretreatment of the host to initiate an inflammatory response or injury at the regenerative site. In addition, pretreatment of the donor cell may also be required. The host may be treated with TNF-α, IFN-γ, IL-2, VEGF, FGF, or IGF-1 to prepare the blood vessel endothelium for optimal interactions with the mobilized Hox 11-expressing cell. Additionally, the pathway of VEGF-stimulated expression on endothelial cells can be enhanced with a selective inhibitor of PI-3'-kinase. Alternatively, the host can be pretreated with platelet-derived growth factor derived from mural cells (e.g., from the neural crest or epicardium) for optimal interactions with the mobilized mesodermal cell. Additionally, the mesodermal cell can be pretreated to optimize adherence to the endothelium. This type of therapy is envisioned to be beneficial for the regeneration of diverse organs or organelles, including islets of Langerhans, liver, pancreas, spleen, and bone.

Other Embodiments

From the foregoing description, it will be apparent that variations and modifications may be made to the invention described herein to adapt it to various usages and conditions. Such embodiments are also within the scope of the following claims.

All publications mentioned in this specification are herein incorporated by reference to the same extent as if each independent publication, patent, or patent application was specifically and individually indicated to be incorporated by reference.

What is claimed is:

1. A method for increasing or maintaining the number of functional cells of a predetermined type in an organ or tissue of a mammal, wherein said organ or tissue is injured, damaged, or deficient in said functional cells and wherein said organ or tissue is, or is part of, pancreas, spleen, liver, kidney, bone, blood, vascular tissue, brain, spinal cord, nervous system tissue, heart, bile duct, skin, bladder, eye, stomach, intestines, muscle, ligament, cartilage, esophagus, gallbladder, lung, ovaries, prostate, testes, thymus, ureter, urethra, uterus, or fat, said method comprising administering to said mammal a composition enriched in pluripotent cells from an adult mammal, wherein said pluripotent cells endogenously express the Hox 11 gene.

2. The method of claim 1, further comprising stimulating said organ or tissue before administering said composition.

3. The method of claim 2, wherein said organ or tissue is stimulated by administering TNF-alpha.

4. The method of claim 2, wherein said organ or tissue is stimulated by administering a TNF-alpha agonist or a TNF-alpha inducing substance.

5. The method of claim 4, wherein said TNF-alpha agonist or TNF-alpha inducing substance is Complete Freund's Adjuvant (CFA), ISS-ODN, microbial cell wall components with LPS-like activity, cholera particles, *E. coli* heat labile enterotoxin, *E. coli* heat labile enterotoxin complexed with lecithin vesicles, ISCOMS-immune stimulating complexes, polyethylene glycol, poly(N-2-(hydroxypropyl)methacrylamide), synthetic oligonucleotides containing CpG or CpA motifs, monophosphoryl lipid A, *Bacillus* Calmette-Guerin, γ-interferon, Tissue Plasminogen Activator, LPS, Interleukin-1, Interleukin-2, UV light, a lymphotoxin, cachectin, a TNFR-2 agonist, an intracellular mediator of the TNFalpha signaling pathway, a NFκB inducing substance, IRF-1, STAT1, a lymphokine, or the combination of TNF-alpha and an anti-TNFR-1 antibody.

6. The method of claim 1, wherein said composition is enriched in cells which do not express CD45 protein.

7. The method of claim 6, wherein said pluripotent cells are enriched from the peripheral blood or tissue of a mammal by a method comprising:
   a) providing from the mammal peripheral blood or tissue that contains pluripotent cells;
   b) separating pluripotent cells from said peripheral blood or tissue;
   c) separating said pluripotent cells into a first cell population which expresses CD45 antigen on the surface of said cells and a second cell population which predominantly does not express CD45 antigen on the surface of said cells; and
   d) selecting said second cell population.

8. The method of claim 1, wherein said pluripotent cells are derived from the spleen.

9. The method of claim 1, wherein said pluripotent cells are semi-allogeneic.

10. The method of claim 1, wherein said pluripotent cells are isogeneic.

11. The method of claim 1, wherein said composition comprises cells that present MHC class I and peptide, wherein said MHC class I has at least one allele that matches an MHC class I allele expressed by said mammal.

12. The method of claim 1, further comprising administering to said mammal an agent that selectively inhibits, removes, or kills cell populations that interfere or prevent the trafficking of, differentiation of, or growth of Hox-11-expressing pluripotent cells.

13. The method of claim 12, wherein said cell populations comprise lymphocytes.

14. The method of claim 12, wherein said agent comprises TNF-alpha.

15. The method of claim 12, wherein said agent comprises a TNF-alpha agonist or a TNF-alpha inducing substance.

16. The method of claim 15, wherein said TNF-alpha agonist or TNF-alpha inducing substance is Complete Freund's Adjuvant (CFA), ISS-ODN, microbial cell wall components with LPS-like activity, cholera particles, *E. coli* heat labile enterotoxin, *E. coli* heat labile enterotoxin complexed with lecithin vesicles, ISCOMS-immune stimulating complexes, polyethylene glycol, poly(N-2(hydroxypropyl)methacrylamide), synthetic oligonucleotides containing CpG or CpA motifs, monophosphoryllipid A, *Bacillus* Calmette-Guerin, γ-interferon, Tissue Plasminogen Activator, LPS, Interleukin-1, Interleukin-2, UV light, a lymphotoxin, cachectin, a TNFR-2 agonist, an intracellular mediator of the TNF-alpha signaling pathway, a NFκB inducing substance, IRF-I, STATI, a lymphokine, or the combination of TNF-alpha and an anti-TNFR-1 antibody.

17. The method of claim 1, wherein said mammal has an autoimmune disease.

18. The method of claim 17, wherein said disease is alopecia areata, ankylosing spondylitis, antiphospholipid syndrome, autoimmune Addison's disease, autoimmune hemolytic anemia, autoimmune hepatitis, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, discoid lupus, essential mixed cryoglobulinemia, fibromyalgia-fibromyositis, Graves' disease, Guillain-Barré, Hashimoto's thyroiditis, hypothyroidism, idiopathic pulmonary fibrosis, idiopathic thrombocytopenia purpura (ITP), IgA nephropathy, insulin dependent diabetes, juvenile arthritis, lichen planus, lupus, Ménière's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis/giant cell arteritis, ulcerative colitis, uveitis, vasculitis, vitiligo, or Wegener's granulomatosis.

19. The method of claim 1, wherein said pluripotent cells are splenocytes.

20. The method of claim 1, wherein said pluripotent cells are obtained from peripheral blood.

21. The method of claim 1, wherein said pluripotent cells can differentiate into two or more different cell types.

22. The method of claim 1, wherein said pluripotent cells are human cells.

23. The method of claim 1, wherein said pluripotent cells express one or more cell markers selected from CD90, CD44, and CD29, but do not express CD34.

24. The method of claim 1, wherein said method comprises administering said pluripotent cells more than once.

25. The method of claim 1, wherein said method comprises administering said pluripotent cells intravenously or intraperitoneally.

\* \* \* \* \*

UNITED STATES PATENT AND TRADEMARK OFFICE
CERTIFICATE OF CORRECTION

| | | |
|---|---|---|
| PATENT NO. | : 8,021,693 B2 | Page 1 of 1 |
| APPLICATION NO. | : 12/549714 | |
| DATED | : September 20, 2011 | |
| INVENTOR(S) | : Denise L. Faustman | |

It is certified that error appears in the above-identified patent and that said Letters Patent is hereby corrected as shown below:

On the Title Page

Under OTHER PUBLICATIONS, in Atkinson et al., replace "Nature" with --*Nature Medicine*--;

Under OTHER PUBLICATIONS, in Mestas et al., replace "pp. 2731-3238" with --pp. 2731-2738--.

In the Specification

Column 1, Line 52, replace "Clamette-Guerin" with --Calmette-Guérin--.

Column 3, Line 32, replace "Clamette-Guerin" with --Calmette-Guérin--.

Column 5, Line 64, replace "Clamette-Guerin" with --Calmette-Guérin--.

Column 24, Line 44, replace "Clamette-Guerin" with --Calmette-Guérin--.

Signed and Sealed this
Twenty-fifth Day of June, 2013

Teresa Stanek Rea
*Acting Director of the United States Patent and Trademark Office*

SEQUENCE LISTING

```
<160> NUMBER OF SEQ ID NOS: 6

<210> SEQ ID NO 1
<211> LENGTH: 27
<212> TYPE: DNA
<213> ORGANISM: Mus musculus

<400> SEQUENCE: 1
cacaagcttg cggccacaca gctctac                                     27

<210> SEQ ID NO 2
<211> LENGTH: 27
<212> TYPE: DNA
<213> ORGANISM: Mus musculus

<400> SEQUENCE: 2
gagggatcca cactctgggt cccagac                                     27
```

```
<210> SEQ ID NO 3
<211> LENGTH: 20
<212> TYPE: DNA
<213> ORGANISM: Mus musculus

<400> SEQUENCE: 3
aagaagaagc cgcgcacatc                                              20

<210> SEQ ID NO 4
<211> LENGTH: 20
<212> TYPE: DNA
<213> ORGANISM: Mus musculus

<400> SEQUENCE: 4
ggagtcgtca gaccacggct                                              20

<210> SEQ ID NO 5
<211> LENGTH: 25
<212> TYPE: DNA
<213> ORGANISM: Mus musculus

<400> SEQUENCE: 5
taaaacgcag ctcagtaaca gtcgg                                        25

<210> SEQ ID NO 6
<211> LENGTH: 25
<212> TYPE: DNA
<213> ORGANISM: Mus musculus

<400> SEQUENCE: 6
tgcaatcctg tggcatccat gaaac                                        25
```